(12) United States Patent
Arnold

(10) Patent No.: US 6,320,931 B1
(45) Date of Patent: Nov. 20, 2001

(54) AUTOMATED X-RAY BONE DENSITOMETER

(75) Inventor: Ben A. Arnold, Columbia, KY (US)

(73) Assignee: Image Analysis, Inc., Columbia, KY (US)

(*) Notice: Subject to any disclaimer, the term of this patent is extended or adjusted under 35 U.S.C. 154(b) by 0 days.

(21) Appl. No.: 09/260,946

(22) Filed: Mar. 2, 1999

Related U.S. Application Data

(60) Provisional application No. 60/076,455, filed on Mar. 2, 1998.

(51) Int. Cl.$^7$ .................................................. G01N 23/06
(52) U.S. Cl. .......................................... 378/56; 378/54
(58) Field of Search ................... 378/54, 55, 56, 378/58, 57, 98.9, 98.11, 98.12

(56) References Cited

U.S. PATENT DOCUMENTS

| | | |
|---|---|---|
| 3,944,830 | 3/1976 | Dissing . |
| 4,593,400 | 6/1986 | Mouyen . |
| 4,721,112 | 1/1988 | Hirano et al. . |
| 4,811,373 | 3/1989 | Stein . |
| 4,829,549 | 5/1989 | Vogel et al. . |
| 4,852,137 | 7/1989 | Mackay . |
| 4,947,414 | 8/1990 | Stein . |
| 5,005,196 | 4/1991 | Lanza et al. . |
| 5,040,199 | 8/1991 | Stein . |
| 5,049,746 | 9/1991 | Ito . |
| 5,122,664 | 6/1992 | Ito et al. . |
| 5,123,037 | 6/1992 | Picard et al. . |
| 5,132,995 | 7/1992 | Stein . |
| 5,138,553 | 8/1992 | Lanza et al. . |
| 5,148,455 | 9/1992 | Stein . |
| 5,150,394 | 9/1992 | Karellas . |
| 5,187,731 | 2/1993 | Shimura . |
| 5,247,559 * | 9/1993 | Ohtsuchi et al. .................... 378/53 |
| 5,335,260 | 8/1994 | Arnold . |
| 5,365,564 | 11/1994 | Yashida et al. . |
| 5,465,284 | 11/1995 | Karellas . |
| 5,577,089 | 11/1996 | Mazess . |
| 5,696,805 * | 12/1997 | Gaborski et al. .................... 378/54 |
| 5,712,892 | 1/1998 | Weil et al. . |
| 5,852,647 | 12/1998 | Schick et al. . |
| 5,902,776 | 5/1999 | Dohner et al. . |

FOREIGN PATENT DOCUMENTS 0253742   7/1987   (EP) .

* cited by examiner

*Primary Examiner*—David P. Porta
(74) *Attorney, Agent, or Firm*—Knobbe, Martens, Olson & Bear, LLP

(57) ABSTRACT

The present invention relates to x-ray analysis apparatus for bone density measurements. Bone Densitometry is the preferred method of diagnosing low bone density such as osteoporosis. The invention is a low cost x-ray bone densitometer capable of measuring bone density in the human body. It is particularly designed to measure the extremities, phalanges, calcaneous or radius, but similar techniques and a modified device could measure in larger body parts. The device can also have application in small animals or animal parts. The use of photodiodes of larger size at fixed locations provides a mechanically positioned Region of Interest (ROI) which reduces software and hardware requirements. The low cost bone densitometer serves as a screening device in primary care physician's offices. The present invention provides a highly automated bone mineral density measurement achieved by simple positioning of the hand, and push button operation. The compact and low cost tabletop x-ray system is powered by line voltage or battery which exposes the body part and calibration phantom or phantoms simultaneously. The device provides exposures at multiple x-ray energies, here introduced as MEXA, (Multiple Energy X-ray Absorptiometry). The invention also utilizes an improved calibration method. This method uses calcium hydroxyapatite in a solid tissue equivalent matrix to form the reference calibration phantom, which is positioned adjacent to the fingers for simultaneous calibration on each exam.

30 Claims, 21 Drawing Sheets

▨ Lead Filled Bronze X-Ray Shield

Densitometer Test System Timing

AUTOMATED X-RAY BONE DENSITOMETER

This application claims priority from U.S. Provisional Application Ser. No. 60/076,455 filed on Mar. 2, 1998 which is hereby incorporated by reference.

BACKGROUND OF THE INVENTION

1. Field of the Invention

A low cost tabletop x-ray bone densitometer capable of measuring bone density in the human body.

2. Description of the Prior Art

Bone density has been directly associated with bone strength and the risk for non-traumatic fractures. Early detection of low bone mass and the application of appropriate therapies is of significant medical value. The ability to monitor therapy effectiveness by detection of small changes in bone density is also of value. Because of the vast need for diagnosis and the high cost of existing devices, there is an unmet need for a low cost bone densitometer with adequate sensitivity for widespread screening of patients at risk for osteoporosis. The immediate readout, low cost, ease of use, and method of calibration provide important advances to the prior art. This invention has the potential to readily provide bone densitometry tests to millions of patients who currently do not, or can not, afford the more involved and costly exams.

Various non-invasive methods for bone density measurements have been developed. These include Quantitative Computed Tomography (QCT), Single Photon and Dual Photon Absorptiometry (SPA and DPA), Dual Energy X-ray Absorptiometry (DXA), peripheral dual energy x-ray absorptiometry (pDXA) and Radiographic Absorptiometry or Micro-densitometry (RA). All of these techniques utilize the difference in x-ray or gamma ray attenuation of bone and soft tissue components. Use of dual energy methods improves on the ability to separate overlying soft tissues from bone in the measurement. The different techniques are largely separated based on the particular bone to be measured and the quantity of surrounding soft tissue. For example, QCT measures the central bone of the spine, which is surrounded by much tissue, while pDXA typically measures the radius, which has little overlying tissue. Osteoporosis is believed to be a systemic disease process, but it is well known that different regions of the skeleton lose bone at different rates.

The QCT method uses a x-ray CT Scanner to generate a cross sectional slice through three to four lumbar vertebra. Typically a bone and tissue equivalent phantom is scanned simultaneously with the patient to provide calibration.

With the SPA and DPA methods, x-rays from a radioactive source such as Gd153 are employed as the source. These methods allow measurements at both the extremities and central skeleton sites and, in the case of DPA, uses dual energy techniques. These techniques have largely been replaced with the newer DXA devices due to the long exam times and need to periodically replace the isotope source.

DXA and pDXA have become widely used in clinical practice. The use of filtered x-ray sources, in place of radioactive isotopes, has improved precision, exam speed and long term reliability. DXA techniques use a scanning x-ray source in a rectilinear fashion to cover the target body part. An image of the body is created showing regions of bone and soft tissue and requires software to find the bone images and edges of bone for measurement. In the DXA approach, the x-ray tube and a point imaging detector are scanned over the target region in a raster fashion resulting in the point-by-point transmission of the beam through the bone and surrounding soft tissue. Point source or more recently fan beam geometries and line detector arrays are used requiring some significant time to complete the mechanical scan. In addition, a mechanical structure is required to reproducibility move the x-ray source and x-ray detectors over the body. The measurement Region of Interest (ROI) is determined in software by finding bone regions. The x-ray source output must be maintained within close limits during the scan, placing stringent electrical stability requirements on both the high voltage power supply and the x-ray tube current throughout the scan. In addition, electrical analysis of pulse height and energy separation is required in the x-ray pulses used to create the images. DXA nevertheless provides bone mineral density, ("BMD"), measurements throughout the skeleton system with low radiation dose and good precision. Whole body DXA devices are expensive and generally require a room size facility for their operation. In response to these limitations, pDXA (peripheral DXA) devices have been developed more recently which are smaller and less expensive. The measurement target is usually the distal radius, although the calcaneous is also measured. One challenge of pDXA devices is the need to reproduce the measured region of interest (ROI) precisely, to maintain high precision in follow up clinical studies. Although of smaller size and lower cost, pDXA devices also use rectilinear scanning techniques as in whole body DXA devices, thus requiring a more complex mechanical design and associated expense. PDXA devices also create an image of the target bone requiring software to define the measurement ROI. PDXA devices require similar controls as the larger DXA machines, on the power supply and detector response over the entire scan time. Scanning pDXA devices remain relatively expensive for widespread clinical use in primary care physician offices.

In recent years, the older technique of microdensitometry has been revived as radiographic absorptiometry (RA). A representative system is marketed by COMPUMED, which provides a mail order service to analyze the x-ray films and provide clinical reports. With RA, a finger bone is exposed simultaneously with a reference aluminum step wedge to x-rays. The image is recorded with direct exposure x-ray film and processed in a standard film processor. The developed films are then scanned with a photo densitometry to record the density patterns of both the target bone and the aluminum step wedge. The aluminum step wedge becomes the calibration phantom for reference to the bone absorption. Although the initial cost to use the service is low (cost of the aluminum step wedge and x-ray film), this approach has several major drawbacks. First, the user must have a complete x-ray system, x-ray generator and x-ray tube, available for use as well as a film processor. These are relatively expensive devices, and are not available in the vast majority of primary care physician offices. The scanning photo densitometer to read the films must have acceptable performance and reliability, thus adding additional costs. Film processors can vary in performance, sometimes producing streaks and artifacts, which need to be accounted for at the film scanning stage. The exposed and processed films must be mailed to a central processing facility, necessitating important delays in obtaining the final clinical results. The use of aluminum to calibrate for bone density is far from optimal. Although aluminum is close to bone in physical density, if differs in atomic composition, and is not an adequate reference for bone for highly consistent results.

Human bone is composed largely of calcium hydroxyapatite in the presence of soft tissue components, blood and fat. The x-ray attenuations of these tissues are dependent on their physical density, their effective atomic numbers, and the energy of the x-ray beam. The x-ray beam spectrum produced by x-ray systems is dependent upon many variables, including the primary kilo voltage applied to the tube, its waveform, inherent and added filtration, x-ray tube target angle, x-ray tube aging and target changes with over exposures, and in some cases, the quality of the line voltage and its stability. In short, x-ray systems from different manufacturers, and in use at different clinics, produce different x-ray beam spectra. These differences in beam energy are important for highly precise quantitative measurements. We have shown with earlier measurements that aluminum may have limitations for accurate calibrations of bone across beam energy changes which may occur with different x-ray systems in use at various radiographic clinics.

The radiation beam in bone densitometers is typically collimated to the desired region of interest before reaching the patient, to reduce radiation dose and improve image quality. Different shaped beams have been used, including pencil beam, fan beam, and cone beam shapes. The beam and the opposing detector should have corresponding geometries. Pencil and fan beam geometry requires scanning, and is coupled to point or line detectors to create images of the bone. Area detectors, such as flat panel silicon arrays, or x-ray film, make it possible to obtain full field area simultaneous exposures of the total body part and calibration reference on a single exposure, and are used in RA techniques, for example, as well as the current invention with modifications.

U.S. Pat. No. 5,365,564, November 94, by Yashida, et al, teaches a method and apparatus for bone morphometry on extremities bones. This method uses x-ray film and illuminating light to obtain morphometric details on bone with semi automatic analysis. The system uses aluminum as the reference standard matter. The system does not propose to measure bone density, and has the undesirable features of using x-ray film and aluminum for reference. U.S. Pat. No. 4,721,112, January 1988, by Hirano, teaches a bone evaluation method that requires determining a bone pattern and calculating a bone index. The bone density distribution is classified by color, and an image is used to produce a bone pattern.

Methods and an apparatus for positioning and placement of measurement regions at a selected distance from a styloid bone tip are taught in U.S. Pat. No. 5,005,196, April 1991, and U.S. Pat. No. 5,138,553, August 1992, by Lanza, et al. The patents employ radiographic imaging devices and describe software methods to reproducibly position ROIs in the images of the radius and ulna. The apparatus employs limb positioning and instrument calibration methods, typically for the wrist, which uses a pair of side blocks and a clamping mechanism to immobilize the limb. The blocks are of different absorptive properties for calibrating the images.

U.S. Pat. No. 5,187,731, February 1993, by Shimura, hereby incorporated by reference, teaches a method for analysis of bone calcium using a plurality of recording media and different kinds of radiation, referenced by a bone calcium material and producing a plurality of radiation images. In one embodiment, a stimulable phosphor sheet is exposed to one exposure of energy A, and thereafter, sheet A is quickly removed from the position for x-ray exposure and stimulable phosphor sheet B is quickly set in place at the same position, for exposure to x-rays of energy B. At the same time, the tube voltage of the x-ray source is changed to produce x-rays of the different energy B. A bone reference material with a plurality of radiation absorption amounts is placed on each of the sheets. The stimulable phosphor sheets are later read out by scanning laser beam deflected by a scanning mirror. The emitted light from the sheet is recorded by a photo multiplier tube, to generate the final electronic image. In a second embodiment, stimulable phosphor sheets A and B are placed one upon the other, and a filter is inserted between the sheets. The filter produces a second, different energy spectrum at the second sheet following a single x-ray exposure. This method has the disadvantage of cost, significant time to change the detector sheets, causing patient motion, and the complex and expensive readout of stimulable phosphors.

Prior art scanning DXA systems, such as U.S. Pat. Nos. 5,040,199 and 4,811,373 to Stein, require multiple reference detectors with differing absorbers are used by the system to continuously correct for variations in voltage and current of the x-ray tube. Stein teaches to insert into and remove from the x-ray beam a piece of bone-like calibration material of predetermined constant thickness, such that the regions of the patient are exposed both to the x-ray beam and to the beam obstructed by said predetermined thickness of bone-like material.

Dissing's U.S. Pat. No. 3,944,830, March 1976, teaches the use of two different photon energies in a scanning apparatus for bone density measurements. Mackey's U.S. Pat. No. 4,852,137, July 1989, discloses an imaging apparatus using x-rays detected by a cooled charge couple device, (CCD), containing two dimensional imaging array of sensors containing numerous pixcels on the order of 250,000 sensor elements which are sensitive to light coupled by a lens to a phosphor, which emits visible light following the x-ray exposure and utilizes a shutter. Mouyen, in U.S. Pat. No. 4,593,400, discloses an x-ray apparatus for imaging which uses an x-ray system, a phosphor screen which converts x-rays to lights, a lens, shielding and collimation, recorded by a charge-coupled device (CCD).

Karallas, in U.S. Pat. No. 5,465,284, November 1995 and U.S. Pat. No. 5,150,394, September 1992, discusses a dual energy system for quantitative radiographic imaging. The system uses an area scanning technique to minimize scanning time. An x-ray source produces two different energy levels from two different exposures, the image is sensed by a scintillator to convert x-rays to light, a lens or fiber optic coupler, shielding, and collimation, recorded by a binnable charge-coupled device (CCD). Quantitative information regarding the object being imaged uses standard dual photon absorptiometry techniques. An internal instrument stability control system provides compensation for any instability in the x-ray tube potential and current. The tube output is monitored by a pair of x-ray sensors placed at a secondary beam port near the tube window.

Weil, in U.S. Pat. No. 5,712,892, January 1998, discloses an x-ray apparatus for measuring bone density of the extremities which uses a calibration wedge, an x-ray image converter, and a digital image processor. Images are produced in an area photodetector array to automatically measure bone density by undisclosed methods.

U.S. Pat. No. 5,852,647 by Schick discusses a method and apparatus for bone density measurements in the hand using hard tissue (aluminum) and soft tissue (epoxy) references. Dual energy exposures are recorded on the area radiation sensor to create high and low energy images. The sensor may be CMOS active pixel sensor arrays, or CCD area arrays, which are optically coupled to phosphorescent material by lens or optical fibers, as in Karellas and other, or are coupled directly on the face of the sensor. In all cases, an image is created which contains an area array of pixels. An iterative process is used to remove soft or hard tissue components to arrive at an aluminum equivalent density. The location of the bones within the image is determined by a thresholding procedure, and the measured region of interest includes any bone region which is positioned and imaged within the sensor's field of view.

All of the above discussed methods either using mechanical scanning or area imaging detectors containing many imaging elements, such as CCD cameras. They require the use of software techniques to detect bone edges from the two dimensional array of pixel elements and to define and locate the ROI of measurement. Measurements are made in bone regions outlined by pixels of varying signal levels defined by software techniques. These methods utilize either single or dual energy x-ray exposures which are calibrated by references placed at the x-ray source or alternatively use aluminum placed in the object plane.

SUMMARY OF THE INVENTION

The present invention provides a low cost tabletop x-ray bone densitometer capable of measuring bone density in the human body. The densitometer is designed to measure the extremities, particularly the phalanges. The invention uses large area x-ray detectors fixed in position and a simplified calibration method which greatly reduces costs and device complexity. The apparatus provides multiple energy x-ray absorptiometry (MEXA) measurements by the use of a bone equivalent calibration phantom exposed simultaneously with the phalanges. The radiation detectors, x-ray source, and calibration phantom are fixed in place to greatly simplify the design and software requirements and thus manufacturing costs. The small x-ray power supply provides multiple beam energies of short exposure times and utilize a mono-unit design where x-ray tube, high voltage and controls are within a shielded container with electrical insulation. Automated software uses fixed locations of components to provide a push button operation. In the preferred embodiment, no image is produced. The large area detectors define the ROI for which the bone density is computed in the microprocessor from measured attenuation values in the bone reference, tissue reference and subject's bone. Bone density in $mg/cm^2$ of calcium hydroxyapatite equivalence and the T-Score are printed on a LCD screen. The system is designed for ease of use, low cost, automated operation, and reliability for expected operation in primary care health clinics.

The invention relates to x-ray analysis apparatus for bone density measurements. Bone Densitometry is the preferred method of diagnosing low bone density such as osteoporosis. The invention is a low cost x-ray bone densitometer capable of measuring bone density in the human body. It is particularly designed to measure the extremities, phalanges, calcaneous or radius, but similar techniques and a modified device could measure in larger body parts. The device can also have application in small animals or animal parts. The use of photodiodes of larger size at fixed locations provides a mechanically positioned Region of Interest (ROI) which reduces software and hardware requirements. The objective of the present invention was a low cost bone densitometer, which could serve as a screening device in primary care physician's offices. The widespread incidence of loss bone density, estimated at 40 million in the US alone, warrants a low cost test that any physician or health care provider can readily use without special training and in their office. We envision this BMD test more like a pressure cuff monitor for high blood pressure, and less like a complicated instrument used only by trained x-ray personnel. The present invention provides a highly automated BMD measurement achieved by simple positioning of the hand, and push button operation. The invention creatively teaches a compact and low cost tabletop x-ray system, which is powered by line voltage or battery which exposes the body part and calibration phantom or phantoms simultaneously. The device provides exposures at multiple x-ray energies, here introduced as MEXA, {Multiple Energy X-ray Absorptiometry}. The invention also utilizes an improved calibration method according to U.S. Pat. No. 5,335,260, (1994, Arnold), hereby incorporated by reference. This method uses calcium hydroxyapatite in a solid tissue equivalent matrix to form the reference calibration phantom, which is positioned adjacent to the fingers for simultaneous calibration on each exam. The small size and simplified push button operation allow its use in doctor's offices without technical training.

More particularly, a preferred embodiment of the present invention defines a multi energy X-ray bone densitometer for measurements of bone density in a portion of the body of a subject including an X-ray source which is fixed in position, a calibration phantom composed of bone equivalent and tissue equivalent materials in regard to X-ray attenuation, wherein the phantom is positioned in a fixed location in the X-ray beam and adjacent to the subject's body such that X-rays passing through the subject's bone do not also pass through the phantom. The X-ray detector of the instant invention comprises a selected number of one or more single discrete photodiode sensors of a large cross-sectional area of from one to twenty-five square millimeters for detecting the x-ray beam transmitted through the subjects body and the phantom. Thus, a preferred embodiment of the detector comprises a single discrete diode sensor as compared to conventional detectors having two dimensional imaging arrays for producing an image. A calibration procedure estimates attenuation coefficients of the phantom for the x-ray beam. An electronic processor is used for controlling the X-ray exposures and analyzing the detector outputs to produce bone density readings in units equivalent to the calibration phantom. The Densitometer also uses an X-ray source which is fixed anode X-ray tube and high frequency high voltage power supply constructed as a single integrated unit with electrical insulation and x-ray shielding.

In a second embodiment, the X-ray detector may include a direct coupled scintillation screen mounted onto a two dimensional solid state detector array of same size, the detector array being formed of amorphous silicon. The calibration phantom has multiple thicknesses of bone and tissue equivalent materials.

Moreover, the dual energy X-ray bone densitometer of the present invention can utilize a dual energy X-ray source comprising a two dimensional area X-ray detector, a bone equivalent calibration phantom, the X-ray source, the X-ray detector and the calibration phantom being fixed in position such that the subject's anatomy to be analyzed and the calibration phantom are exposed simultaneously in one X-ray exposure of first X-ray energy and exposed simultaneously in a second X-ray exposure of second X-ray energy. The detector produces quantitive electronic representations from detected x-rays which have penetrated the phantom or the subject's anatomy. The fixed locations being used to automatically locate measurement regions in the resultant electronic representations. A computer processor and operating software is used to determine bone density of the subject's anatomy in an electronic result.

Another aspect of the invention is a method to test functionality of the X-ray bone densitometer comprises an X-ray source, X-ray detector, and a bone equivalent calibration phantom of at least one thickness. The X-ray source, the X-ray detector and the calibration phantom are fixed in position such that the subject's anatomy to be analyzed and the calibration phantom are exposed simultaneously in one X-ray exposure of first X-ray energy and exposed simultaneously in a second X-ray exposure of second X-ray energy. Electronic representations from x-ray attenuation in the phantom are used to test the functionality of the densitometer for errors. A computer processor is used to perform the tests and display the errors. The densitometer functionally testing can also includes measurement of x-ray beam energy. The functionally testing also can include signal noise related to X-ray source output or detector noise. The testing includes establishing a preset exposure level transmitted through preselected phantom step thickness to normalize exposures at each exposure energy.

Furthermore, the present invention provides for a bone densitometer method for quantifying bone density in a living subject using a projection x-ray imaging system and a calibration reference phantom, comprising the steps of placing the phantom adjacent to a portion of the subject wherein the phantom having one or more effective thicknesses of substantially tissue equivalent material with respect to x-ray attenuation properties and the substantially tissue equivalent material having calcium blended homogeneously therein so that the effective thicknesses of the phantom provide one or more calibrations; creating images of the phantom and the portion of the subject simultaneously using one or more x-ray exposures with an x-ray imaging detector; and comparing the images of the phantom and the portion of the subject electronically to quantitatively determine bone density in the subject in units equivalent to the calibration phantom.

BRIEF DESCRIPTION OF THE DRAWINGS

A better understanding of the present invention will be had upon reference to the following description in conjunction with the accompanying drawings in which like numerals refer to like parts throughout the several views and wherein.

SPECIFICATION

Figure 1:
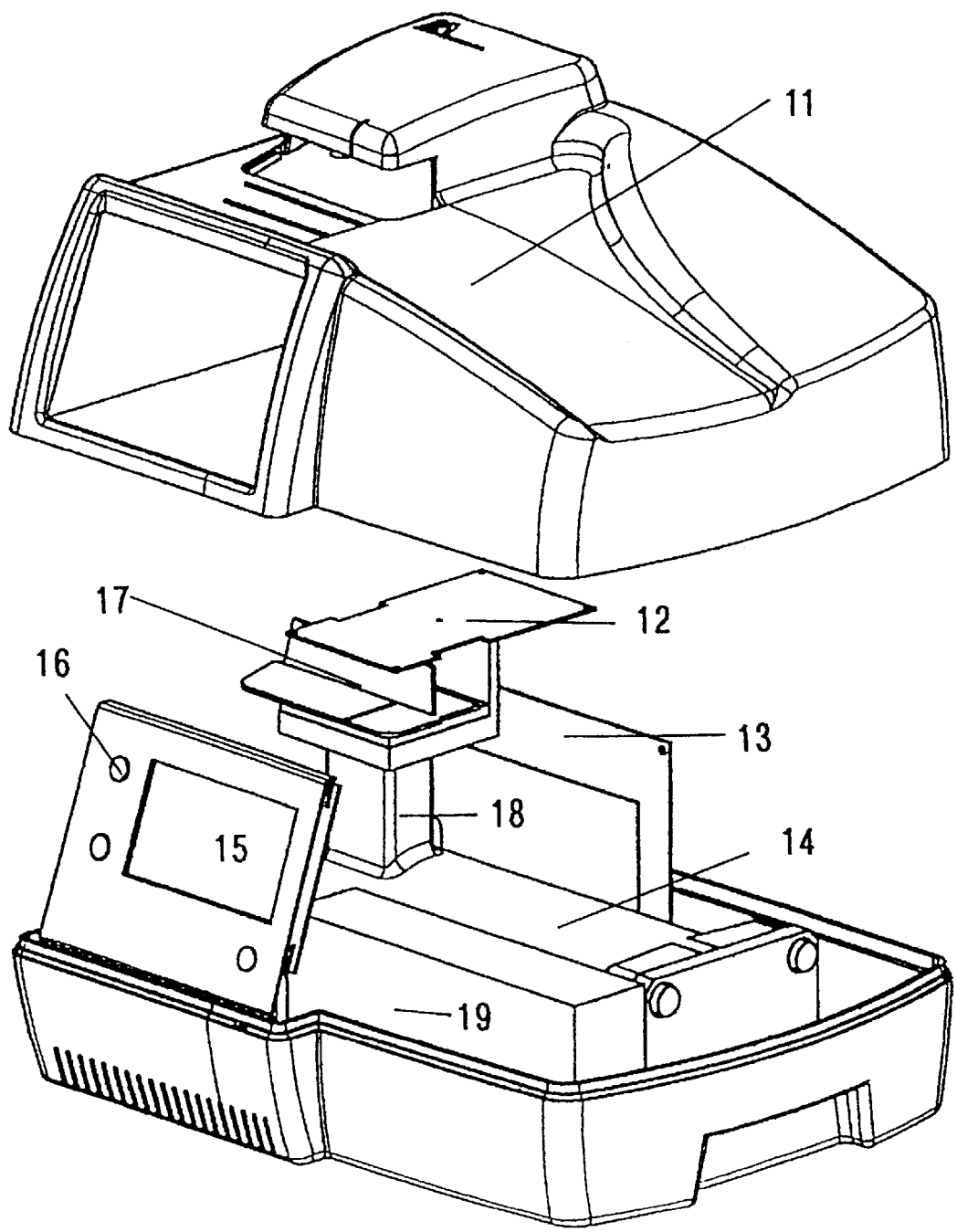
FIG. 1 shows a surface rendering of the bone densitometer utilizing the preferred embodiment.

The bone densitometer of the present invention utilizes novel designs and new techniques to achieve the desired objective of low cost and ease of use. The use of multi energy x-ray exposures and large size discrete x-ray detectors at fixed positions greatly simplifies design. Simultaneous calibration in the object plane with highly equivalent bone and tissue references greatly reduces the stability requirements on the x-ray power supply. The photon energy spectra and reproducibility of beam energies need not be highly controlled. The device uses a small, low cost kVp switching x-ray source, a fixed positioning structure for the phalanges, calibration software utilizing fixed mechanical ROIs, a QA and error detection software procedure, discrete, large size photodiode detectors in one embodiment and in a second embodiment a flat panel imaging x-ray detector, a push-button automated exposure and analysis scheme, and simple, fast electronic readout of the BMD values. The device can readily be operated by untrained personnel in offices, drug stores, or other healthcare facilities.

According to one aspect of the invention, a compact, low cost, x-ray power supply for x-ray generation is provided. The x-ray exposure requirements for tube current are low for the extremities, particularly the fingers. Further advantages of using the fingers are minimal patient motion, and a well-defined bone with clear demarcations. A small x-ray tube with microfocus size of less than 1 mm diameter reduces cost and allows close positioning of the x-ray tube to the detector to reduce x-ray output requirements. The entire x-ray source is housed in one x-ray shielded enclosure of integrated design, filled with electrical insulation to reduce size, cost, and provide long term reliability. Insulation in one design may be gas at increased pressure, which has the added advantage of reducing attenuation and scatter of x-rays before exiting the tube structure, as in the case with oil insulation. This integrated mono unit design minimizes or eliminates concerns for electrical safety, while reducing costs due to the absence of a high voltage cable and lack of accidental contact to high voltage components. The unit is therefore safe for general use with minimal maintenance requirements. Should the system fail, the entire unit can be readily shipped for easy replacement. The mono unit design provides x-ray shielding in a low cost manner, due to its small size. The instantaneous power requirement to the transformer is provided by a 24-volt DC power supply, and therefore high voltage exists only inside the mono unit, which is well insulated. The DC power supply or battery charger is powered from a common 85/230-volt AC outlet. The battery provides sufficient stored power for several x-ray exposures, making the device truly portable, and useable, even in the absence of AC power. Use of the battery also assures consistent power to the transformer, even in the presence of line voltage fluctuations, since these would only be present in the battery charging operation. The advantage of the battery design for a low-cost bone densitometer can also have potential use in larger, higher cost bone densitometers. Using the battery as the primary source of voltage to the high voltage transformer could reduce the need for precise regulation of high voltage and current required in conventional densitometers powered from AC lines.

Figure 16:
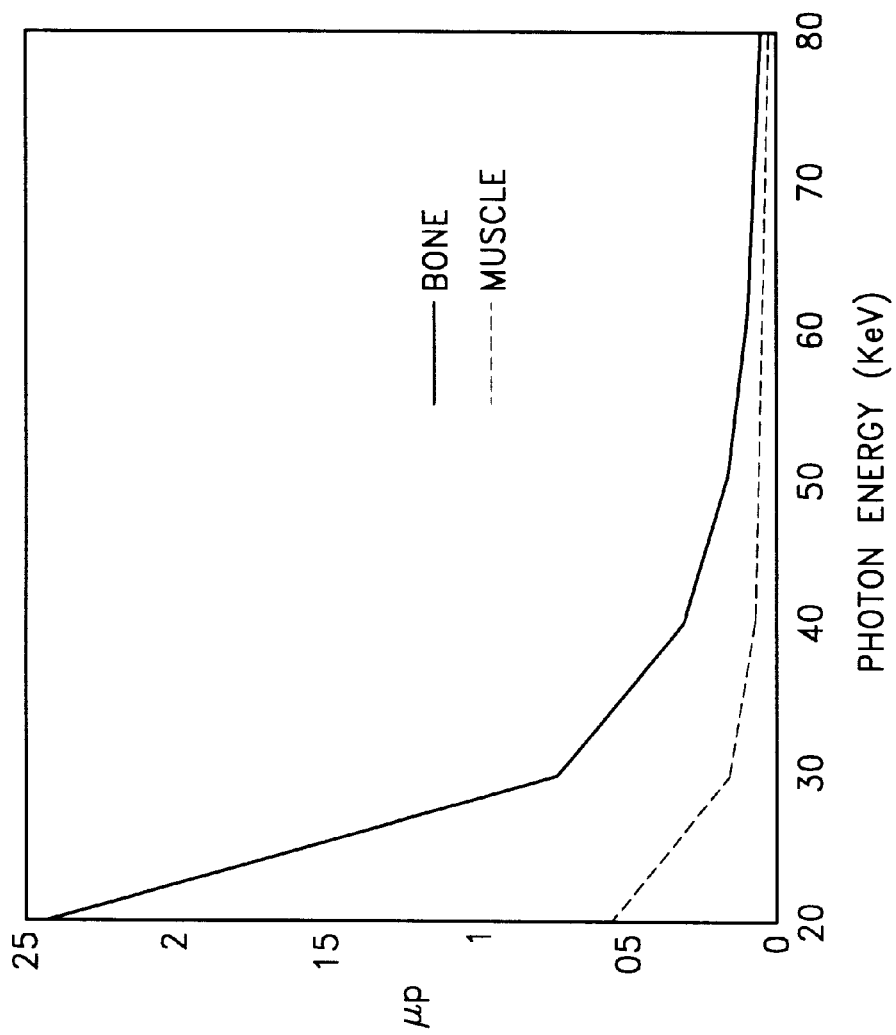
FIG. 16 is a graph showing the mass energy absorption coeffficients of bone and muscle.

In another aspect of the invention, dual energy measurements are made in one continuous, varying x-ray exposure, made without turning off the x-ray power supply. The two energies are obtained with minimum time separation, and are made reproducibility on each patient. The energy exposures are activated by a single push button operation, under microprocessor control. The x-ray energies are further achieved by the use of a fixed, constant x-ray filter, which avoids the need for mechanical means to switch filters during x-ray exposures, or timing of kVp changes with filter placement. The design is therefore simplified while achieving sufficient energy separation in the x-ray spectral distributons, which is further improved by the use of k-edge absorption, which is widely known in the field. Such filter is selected to preferentially absorb x-ray photons of undesirable energy, while passing those of preferred energy. Since the filter is fixed in location, the filter must be selected to provide useful filtration at both energies. It is desirable to have sufficient energy separation in the determinations to optimize the separation of bone and soft tissue. The x-ray attenuation of bone and tissue is photon energy dependent, as the attenuation coefficients vary significantly with the energy of the exposing x-ray beam, as illustrated in FIG. 16. The x-ray exposure is initiated at the high kVp of about 60 kVp, and switches automatically to the lower kVp under microprocessor control.

The fixed filter is chosen to absorb higher energy photons in the low energy spectrum, and lower energy photons in the higher energy spectrum. A filter such as tin, with k-edge at 29 KeV, or elements of nearby atomic members, is chosen due to availability. A combination of two filters has some advantages, such as examples of Sn+Cd, Sn+Ag, Sn+Mo, Sn+Copper, etc. A filter thickness on the order of 100 mg/cm$^2$ of tin is employed. The separation of absorbed, effective photon energies is further improved by the selection of the primary detector material, preferably an x-ray phosphor, and its thickness. The x-ray phosphor also has a K absorption edge leading to preferential absorption of x-rays above its k-edge energy. One selected phosphor is composed of gadolinium oxysulphide ($GdO_2S$), which has its k-edge at 50.2 KeV. $La_2O_2S$, with k-edge at 38.9 KeV, may also be used to advantage, or as a combination of the two phosphors. The absorption properties of the x-ray phosphors are chosen with k-edge to selectively absorb higher energy photons above the k-edge energy when the x-ray tube is operated at the higher kVp. This selective energy separation achieved by the phosphor, works only if the phosphor thickness is chosen to absorb only a fraction of the incident x-rays. That is, if the phosphor is made thick, it eventually absorbs all of the incident x-rays of all energies, losing the energy selective advantage of thinner phosphors. Computer simulation calculations of various filters and filter thicknesses, various phosphors and phosphor thickness, object thickness and kVps were carried out to find optimum combinations which could provide acceptable energy separation. This avoids having to change filters during exposures, and thus reduces expense and complexity. This analysis shows a phosphor of about 80 mg/cm$^2$ thickness of $GdO_2S$ achieves sufficient separation at kVps of 40 and 65 when filtered with 100 mg/cm$^2$ of tin. Multi-energy quantifications can thus be achieved without filter change, and during a contiguous x-ray exposures of 30 to 65 kVp, without turning off the high voltage or interrupting the one continuous x-ray exposure. The x-ray generating means of multi energy is thus creatively achieved with simplified and inexpensive methods.

In the preferred embodiment of the invention, multiple energy measurements are made in one continuous varying x-ray exposure without turning the x-ray source off, here called multiple energy x-ray absorptiometry (MEXA). The use of 4 x-ray energies are employed in one design of approximately 60 KV, 50 KV, 40 KV and 30 KV. The multiple x-ray energies aid in separation of the influence of overlaying tissue and/or fat on the bone measurement. Multiple energies allow the generation of an attenuation curve fit to the 4 data points at 4 energies on both the bone and tissue equivalent calibration phantoms, which further uniquely define an exact combination of bone and soft tissue thicknesses at the measured area of interest. Differences between the measured outputs at the different energies can be used, as the calibration data, in place of the unsubtracted outputs, thus avoiding the influences of detector drift, energy drift, temperature drifts or other changes in sensitivity of the detectors, etc. This provides for more robust results independent of hardware changes. The multiple energies are initiated from a single push button operation and in close time sequence to avoid patient movement. The multiple energy approach (MEXA) is initially used with discrete large area photo diode detectors, which have high sensitivity to x-rays, although this method can also be used with the area silicon imaging array detectors as well.

In another aspect of the invention, calibration means and positioning is achieved to provide reproducible results with the low cost x-ray system and without the conventional methods of scanning and pulse height analysis or highly separated x-ray pulses in energy. The bone and tissue equivalent calibration phantoms and calibration method has been disclosed previously in U.S. Pat. No. 5,335,260 issued to Arnold. Each phantom provides multiple calibrations of varying effective thicknesses of calcium hydroxyapatite or tissue equivalent material. The phantoms are formed of a material which is highly stable, being formed of a solid resin matrix which is tissue equivalent in terms of x-ray attenuation. The phantom is exposed simultaneously with the body part, preferably the finger. Since x-ray attenuation is energy dependent and the low cost design does not provide highly stable controls on high voltage and tube current, the phantom provides a simple and reliable way to achieve highly consistent results. It is well known that beam hardening occurs with different size patients or absorbers, which leads to a shift in x-ray beam energy. It is well known that x-ray tubes age, pit and produce shifts in beam energy output from tube to tube and over time. Conventional bone densitometry methods require highly stable x-ray systems (or alternatively require x-ray sensors at the beam port of the tube housing, such as U.S. Pat. No. 5,465,284), to monitor beam energy shifts to allow corrections to quantitative information, using dual photon absorptiometry techniques. The current invention uses calibration techniques differing from DXA, pDXA or RA. The current technique accomplishes calibration by use of a bone equivalent phantom positioned in the plane of the body part. The calibration phantom is placed in close proximity to the body part, and in a fixed constant position. This is important for consistent results, since the beam energy varies at different locations in the two-dimensional x-ray field provided at the tube output. This variation depends on x-ray tube target angle, tube aging and scatter and off-focus radiation. By analyzing a small body part, and placing the calibration phantom in the plane of the body part and closing adjacent, the area of measurement is greatly reduced to a size of about 1.5×1.5 inches. Beam energy variations within this size field are small, and will not significantly effect the results. The finger is reproducibly positioned on repeat exams, and from patient to patient, and the calibration phantom is constantly fixed at one location, such that relative quantifications of the target bone and the phantoms are consistent over time. The phantom is formed of a calcium concentration, size, and thickness to approximate the target bone of the middle phalanges. Beam hardening, scatter and geometrical effects of focal spot blur, and edge effects are quantitatively similar in the bone and the phantom. In one embodiment, a second calibration phantom (wedge) is soft tissue equivalent, and is exposed simultaneously and adjacent to the bone phantom and subject. This phantom allows precise estimates of x-ray attenuation for soft tissue for the various x-ray beam energies used. The phantoms highly approximate the attenuation of the patient's bone and soft tissue such that shifts in beam energy will produce equal attenuation effects in the patient and the phantoms. The location of the phantom and bone are fixed in position relative to the x-ray field, and also relative to the detector location. Detector sensitive, stray x-ray or optical radiation, or other spatial variable in the detector plane will therefore be constant. The calibration method and the fixed locations greatly reduce the requirements on high voltage and tube current stability relative to other bone densitometers.

The calibration phantoms are manufactured in large, controlled lots, and produced with close tolerance on equivalence to each other. Therefore, measurement results on different BMD units, and at different clinics, will be consistent. This is an important limitation of all current BMD devices, as clinical results are not equivalent for different manufacturers' devices, different techniques, or at different diagnostic centers. Currently, a patient under drug therapy for osteoporosis, for example, can not be re-examined later, at a different location, and expect adequate precision to determine if the therapy is effective. Because of the design of the current invention, and the absolute consistency of the calibration phantoms, equivalent readings are expected among all clinical sites that use this device.

The examination of small body parts, such as the middle phalanx or the second finger, is important to the design of the current invention. The small body part allows a large reduction in the x-ray field size, reduction of required tube current, reduction of high voltage, reduction of scattered radiation, reduction of beam hardening, and provides consistent beam energy throughout the small field, etc., all allowing a low cost and simplified design. The reduction of scatter radiation is an important design advantage. Scatter radiation increases with both the area of the x-ray beam, and the thickness of the body part. The use of pencil scanning beams or fan beams is required for scatter reduction for conventional DXA devices in addition to other reasons. Other methods use air gaps or lead grids to remove or reduce scattered x-rays before it reach the detector plane. The air gaps require smaller focal spot x-ray tubes with rotating anodes to achieve acceptable resolution, and thus greatly increase the cost to build such a device. This Scatter can be very high when a large area of tissue and bone is imaged at an anatomical location in the torso, where tissue thicknesses can be 20 to 40 cm. Beam hardening and scatter become major limiting factors in this body region, which must be overcome to achieve highly consistent results. Accuracy and precision can be greatly compromised due to the presence of scatter radiation relative to conventional scanning DXA devices. A fixed template aperature is positioned between the x-ray source and the finger areas and calibration wedges. This aperature limits the beam to only those areas which can expose both the detectors, the wedges, and bone target region.

In another aspect of the invention, a support surface is provided for the left hand, with positioning elements to isolate the first digit from the thumb and other fingers. The surface provides a reproducibly position for the fingers, and at a fixed distance from the x-ray source. The positioning elements reproduce the location of the middle phalanges on all patients, and on repeat exams of the same patient. The surface has a preferred area of reduced x-ray absorption above which the calibration phantoms and subject's finger are placed, to reduce x-ray exposure and scatter.

In the preferred embodiment of the invention, single large area x-ray detectors are positioned in fixed locations above the patient's phalanx. The detectors consist of a photodiode of known, fixed area, such as 5 mm by 5-mm surface area. The diode is highly sensitive to light and is covered by an x-ray phosphor, such as CsI or $GdO_2S$. The phosphor absorbs the incident x-rays, producing light, which is detected by the diode. The diode/phosphor's active area is greatly larger than an imaging element or pixel of an imaging detector such as a CCD or flat panel amorphous silicon detector designed for imaging. The use of a relatively large area, single detector without imaging capability, has several advantages. The area of the detector defines the area of measurement (ROI) defacto, thus avoiding the need for software to define and position ROIs in the bone image, or to automatically locate the edge of bone images. This greatly simplifies the device operation. The use of discrete, low cost photodiode/phosphor combinations avoids the need for an imaging detector, which further reduces cost and instrument complexity. This embodiment requires no image to be generated, analyzed, or stored, thus simplifying the electronics to a microprocessor, such as the Motorola 68HC16, with 10 bit analog-to-digital converter. Further the ADC need not be fast, as a small amount of data is generated from the single diode detector, in sharp contrast to the approximately 250,000 detector pixels employed with a 512×512 CCD camera. Data storage and processing is likewise reduced. Image analysis software and autodetection routines for the bone, ROIs and calibration phantom steps are obviated.

The single detector diode system has the disadvantage that the ROI, in this case the diode itself, requires manual placement relative to the subject's finger bone. This placement must be certain, and must assure that the entire photo diode is covered by bone and not partial volumed with bone and the surrounding tissue. A method to achieve this is described further below. The single photo diode detector has the added disadvantage that the exact ROI placement within the bone can not be ascertained, but only that the ROI is within the bone region. Therefore, this embodiment of the device can not be assured of high precision on repeat measurements. Its major use is expected to be for screening, where high accuracy for bone density measurement at the defined bone location is achieved. Bone density is calculated in the results, using the known area of the photo diode/phosphor as the ROI area for density calculations. The diode sensitive area, corrected for the known, fixed magnification, defines the measured bone area.

Location and positioning of the subject's bone relative to the fixed location of the photodiode/phosphor detector is achieved by manual means. It is desired to position the diode area within a region of the middle phalanx, composed primarily of trabecular bone, and near the distal end of the bone, and not within the finger joint. Two methods are used to accomplish this with high certainty. First, the detectors are fixed in position above a locating marker or edge, over which the fingers are positioned. The marked surface and grooved finger channels locate the finger bone over the diode detector with approximate positioning. Secondly, although a single photodiode/phosphor of about 25 $mm^2$ area is used for the measurements, 6 similar detectors are positioned adjacent and near each other in 2 offset rows of 3 detectors each. The 6 diodes can be positioned with confidence, such that at least one detector is completely covered by bone. The six readouts are evaluated for the one with the lowest reading, i.e., it must then be located behind the most bone. This diode is selected for the measurement results. A diode which partial volumes bone and tissue will produce a larger signal due to the lower attenuation of tissue compared to bone. Should one row become positioned behind the joint or behind the central region of the phalanx with increased cortical bone, this diode will necessarily have to include some soft tissue, and will thus produce detectable varying readings as well. The two central diodes will be expected always to be covered by bone because of their size and fixed location. Software test algorithms are developed to test various criteria for selecting the optimum detector for final data analysis.

In another preferred embodiment of the invention, a small area imaging detector is used to record the quantitative determinations. Since the body part is small, the detector array can be of small size, and with modest pixel resolution. Pixel resolutions of 512×512 or less are adequate for the small field of 1.5 inches. The cost of the detector can therefore be greatly reduced over what would be required for the spine or hip, for example. The thin body part allows the detector sensitivity to be low, also, further reducing the detector requirements. The detector can be the newer, flat-panel amorphous silicon detectors, which capture images digitally, such as that of dpix of XEROX corporation, or that of EG&G Reticon. CANNON and TREX MEDICAL offer other silicon detectors. Detectors based on charge coupled devices (CCD) technology are available from SWISSRAY, OLDELFT, KONICA, TREX MEDICAL, TROPHY, and other mammography and dental radiography companies. Both CCD and amorphous silicon sensor arrays utilize an x-ray phosphor in front of them to convert the x-ray to light. The flat-panel detectors have the advantage of being of larger area, on the order of the anatomy of the target body part, thus allowing direct contact coupling of the phosphor to the silicon area detector. This avoids the need for lens or fiber optic coupling, while providing higher sensitivity. CCD detectors require the optical image from the phosphor screen to be greatly reduced in size, to match the much smaller CCD array. CCD detectors have been used for many years, such as in the THROPY dental system, and U.S. Pat. No. 4,593,400, June 1986, by Mouyen, both hereby incorporated by reference. Other detectors, such as flat panel detectors with selenium or stimulable phosphors, such as in U.S. Pat. No. 5,187,731, by Shimura, are not acceptable for the dual energy methods with the currently disclosed fixed filter and simplified x-ray system, since the two energies need to be obtained with a fast read out time to avoid motion. The current invention, in one embodiment, uses a $GdO_2S$ phosphor screen, readily available from KODAK at low cost. The detector requirements need to be a rapid readout, sensitive to an appropriate phosphor, with desirable k-edge, and of sufficiently low cost.

In another aspect of the invention, using the area array detector embodiment, auto analysis software is provided which utilizes the known, fixed location of the calibration phantoms, known location of the finger, fixed and stationary location of the x-ray source, patient support surface and detector location, all to advantageously placed regions of interest (ROI) for automated bone density analysis. Search routines to locate the phantom and different phantom step thicknesses can be greatly simplified because of the known locations, object sizes, and shapes. The finger bone is identified in the field of view from its relative location adjacent to the fixed phantom and anticipated attenuation values. Once the finger is located, an edge locating algorithm is used to find the bone edges, or alternatively, the entire bone area is analyzed with a histogram to identify cortical and trabecular bone regions and to calibrate these to the reference wedges. The entire middle phalanx of the second finger may be used in the quantification or smaller different ROIs equally well localized. Use of the entire bone improves reproducibility, such that repeat measurements will locate the same regions of the bone, thus increasing measurement precision. Use of a complete, well demarcated bone overcomes the difficulties of ROI placement in other bone densitometers, such as the distal radius of the wrist in the methods of Lanza U.S. Pat. No. 5,138,553, August 1992, which requires identification of the styloid bone tip, and arbitrary placements to achieve acceptable reproducibility of the measurement ROI on repeat scans.

In another aspect of the invention, means are provided to monitor the device performance and to routinely perform QA checks on the system. The relative attenuation of the calibration phantom steps is used to measure a parameter related to effective beam energy. The slope of the attenuation curve obtained from measurements made behind each phantom step can be directly related to beam energy and can be used to monitor x-ray tube beam energy over time. The absolute intensity of x-rays penetrating a fixed step of the phantom provides a measure of tube radiation output. Variations in this measurement can be related to a failed tube, target pitting, tube position shift, etc. The noise in a ROI behind the phantom or in one photo diode can be used as a test of detector noise, detector temperature shifts, low radiation output, etc. The fixed phantom location and constant, stable phantom provides a convenient method for QA device monitoring or instrument error detection should the device malfunction. The measured parameters can be used in a diagnostic way to aid the user, as well as to support device servicing and manufacturing acceptance testing.

In another aspect of the invention, bone density readout in $mg/cm^2$ calcium hydroxyapatite equivalents is provided immediately on an LCD display along with a calculated population reference to normal patients, such as the T-Score proposed by the WHO as a comparison to young normal patients. The display is configured to also provide access to the QA data and test results as discussed above. The display allows for patient sex selection, to allow T-score calculation based on sex matched young normal data input. The processor will hold reference population data in storage for the clinical calculations and reporting. The BMD device will be contained in housing for transporting, and will contain AC power cabling. Ready, expos and other device functionality indicators are provided. The entire device is controlled by a microprocessor, such as the MOTOROLA 68 HC16 which performs the calibrations, displays results, shows device status and retains reference data for the T-Score calculation. Flash memory as well as RAM memory is provided in the main processor board. A serial data port is provided to an independent PC computer with database for those wishing to print a detailed clinical report with normal reference graph or other diagnostic information.

In the case of the preferred embodiment of the invention, using single discrete detectors, the measurement ROI is defined by the sensitive area of the detector. For this embodiment, no automated software is required to locate the bone or the measurement ROI. Four x-ray exposures at four (4) distinct x-ray energies are made, and read out through the ADC to the microprocessor. The four x-ray exposures can be used to define a unique x-ray attenuation curve verse energy for both the known calibration phantom steps of the bone and soft tissue phantoms, and for the unknown patient use. By simple mathematical analysis a unique solution of bone content and soft tissue content can be defined using the measured values from the known phantoms. By using the area of the discrete detector, an areal bone density in mg/cm² of calcium hydroxyapatite equivalence can be calculated, as referred to the bone equivalent calibration phantom.

The first quantitative determination at first beam energy and second quantitative determination at second beam energy are subtracted and normalized using the calibration phantom as reference. The resulting difference values from the ROIs of the phantom and the ROI of the target bone are calibrated in mg/cm² of calcium hydroxyapatite, using the known concentrations in the phantom. In the first preferred embodiment, the calibration curve is not shown, and images are not produced or output for display.

Some elements of the present invention can utilize other x-ray detectors, such as two x-ray films or x-ray screen-film combinations separated by a filter, or by exchanging detectors between exposures or the use of stimulable phosphor plates, as set forth in the Shimura while maintaining many of the advantages of the current design. Those skilled in the art will recognize other detector combinations that could achieve the required quantifications.

During use of the device, the operator is required to select the patient's sex, position the hand and finger on the supporting surface and then push the exposure button. The device is x-ray shielded to allow its use in non-controlled radiation areas, such as doctor's offices. The device can be readily picked up and moved from area to area and operated from a common wall AC electrical outlet, or, alternatively, with a battery, making it highly portable.

BONE DENSITY CALCULATION

The bone density in a target ROI in the subject is calculated from both known quantities and measured signals from the detectors. The known quantities are the concentrations of calcium hydroxyapatite, the step thicknesses of the bone phantom, the step thicknesses of the tissue phantom, the beam kVps, and anticipated effective attenuation ranges, exposing magnifaction and the area of the detector. The measured quantities include the detector signals from each of the individual detectors at each of the exposing kVps, totaling up to 33 to 64 individual readings.

Representative calculations of the first embodiment can be demonstrated by considering only the reference calibration wedge. It is understood that a linear ramp wedge or wedges with different numbers of steps may be used. The example uses only one wedge of four step thicknesses.

Figure 17:
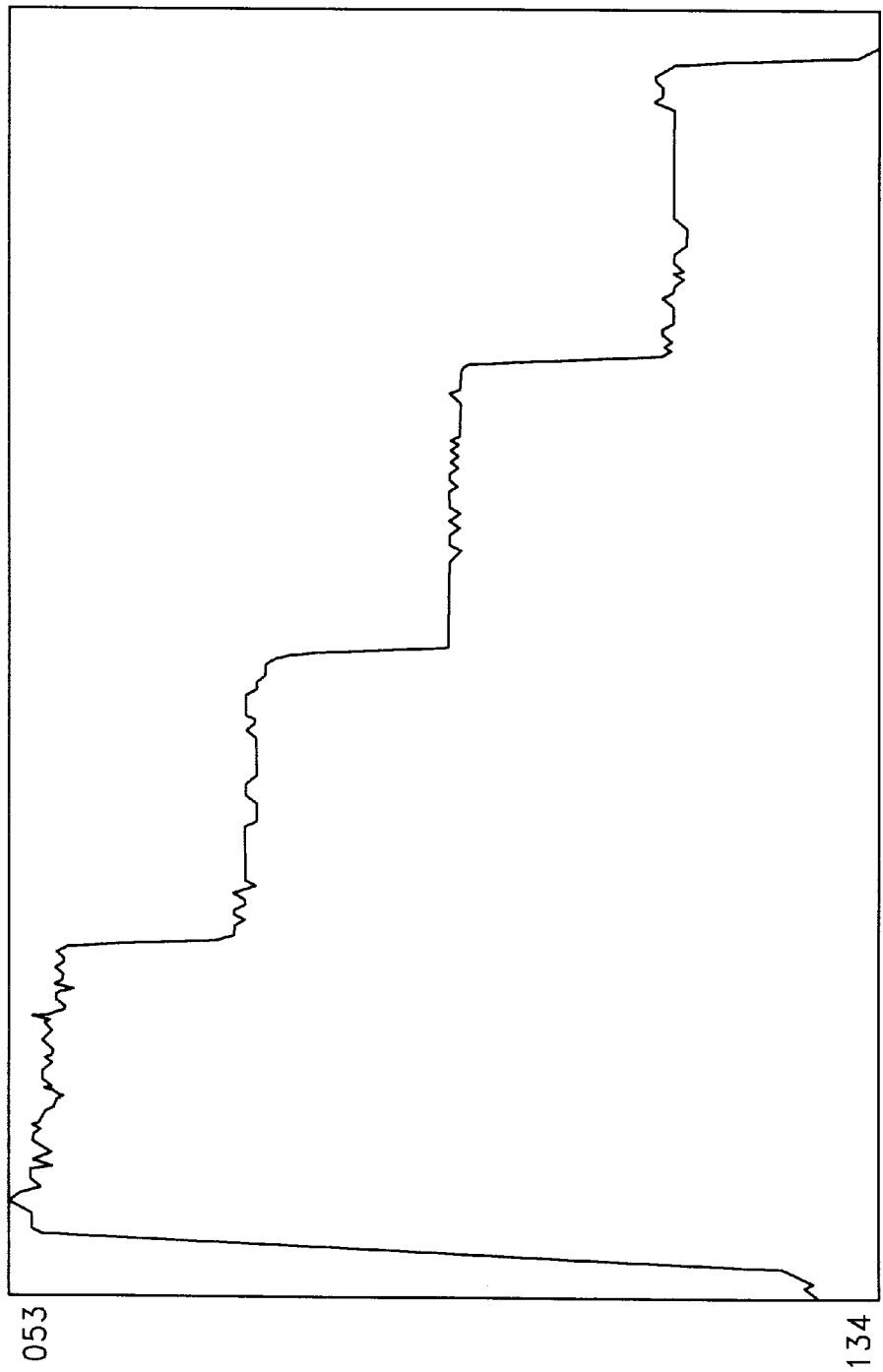
FIG. 17 is a graph showing a reference calibration wedge for the bone density in a target ROI.

Attenuation through an object of thickness X with a monoenergetic x-ray beam of energy E and attenuation coefficient of $\mu E$ is given by the usual relationship:

$$I = I_o \, e^{-\mu(E)X} \qquad (1)$$

Where I and Io are the transmitted intensity and the exposing intensity, respectively. As the known thickness of each step increases, the transmitted x-ray intensity decreases. The transmitted intensity through a four step calibration wedge is shown in FIG. 17.

Since the x-ray beam is not monoenergetic, the exact values of $\mu$ at energy E is not known, and must be estimated from the measured values of the detector readings behind each respective phantom step. Also, as the step thickness increases, beam hardening leads to a shift in the beam spectra seen at the exit of each step. The detector readings will be used to calculate the "effective" $\mu$ at each energy (E) through each phantom step (X).

In order to normalize the results, the difference in attenuation between neighboring steps can alternatively be used to estimate $\mu'$ (E) effective.

$$\ln I_1 - \ln I_2 = \mu'_{EFF}(E)(X_2 - X_1) \qquad 2)$$

where $I_1$ and $I_2$ are transmitted intensities and $X_2 - X_1$ is the difference in step thickness.

Then:

$$\mu'(E) = \frac{\Delta \ln I_n}{\Delta X}$$

3) Equation 3 is used to determine the effective attenuation coefficients $\mu'$ (E) through each phantom step and at each of the exposing beam energies, and repeated for the tissue phantom wedge.

The subject's body part contains both soft tissue components of thickness ($T_s$) and bone of thickness ($T_b$), and physical densities ($\rho$). The transmitted intensity of the body part is then:

$$I = I_o \, e[-\mu_b \rho_b T_b + \mu_s \rho_s T_s)] \qquad 4)$$

$$\ln I_o/I = \mu_b \rho_b T_b + \mu_s \rho_s T_s \qquad 5)$$

Where $\mu_s$ and $\mu_b$ are mass attenuation coefficient and $\rho_s$ and $\rho_b$ are the densities for soft tissue and bone respectively, and $T_b$ and $T_s$ are unknown thicknesses of bone and tissue. Ln Io/I will be measured at each exposing beam energy, and $\mu_b$ and $\mu_s$ will be estimated with high accuracy from the measurements on the bone and tissue wedges. Note that ln Io/I, $\mu'_b$ and $\mu'_s$ will change with beam energy and object thickness and it is this change which provides a unique solution for the thickness and bone density.

The difference in x-ray transmission through the subject between two beam energies is given by $$\ln I(E_1) - \ln I(E_2) = \rho T_b(\mu_b(E_1) - \mu_b(E_2)) - \rho T_s(\mu_s(E_1) - \mu_s(E_2)) \qquad 6)$$

$$\Delta \ln I(E) = T_b(\text{g/cm}^2) \cdot \Delta \mu_b(E) - T_s \text{g/cm}^2 \cdot \Delta \mu_s(E) \qquad 7)$$

Repeat measurements at the four x-ray energies will lead to three sets of values for equation 7. The thicknesses in g/cm² for bone ($T_b$) and soft tissue ($T_s$) will be selected for the result which best fit the equation 7 equality at different x-ray energies.

Bone mineral content (BMC) is given by $$BMC = BMD \cdot Area \qquad 8)$$

where BMD is bone density in g/cm² and Area is the area of the detector sensor in cm² which is fixed and defined by the detector as previously discussed.

Application of the above-described invention is better understood with reference to the drawing FIGS. 1–15 as follows:

FIG. 1 shows a surface rendition of one design of the bone densitometer using the preferred embodiment. The top housing cover contains the support and positioning surface (11) for the left hand. The index finger is placed under the detector board (12) containing the discrete x-ray detectors positioned in a fixed pattern. The finger is aligned with a marker to position the knuckle and the finger against a covering of the calibration wedges not shown. The main processor board (13) is positioned vertically to save space. The x-ray source (14) is enclosed in a shield container including the collimation (18) and containing the beam exit aperature and fixed filter (17). The 24V-power supply or battery (19) is connected to an A-C power cord. The LCD display (15) will show bone density readings, patient T-scores, device test data and error check messages. The exam is initiated by a single button push for female or male (16) patients.

Figure 2:
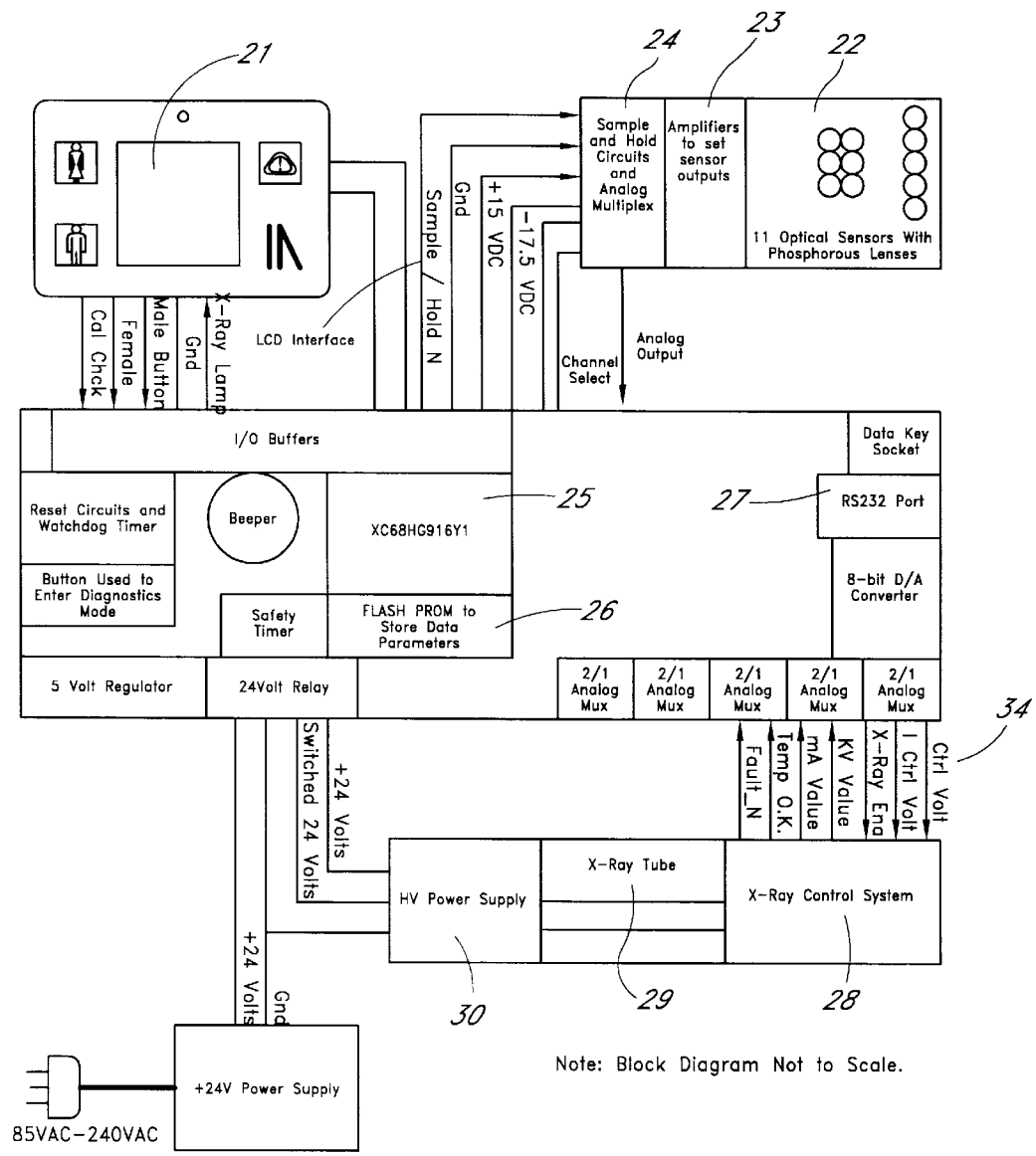
FIG. 2 is an electrical block diagram showing the key elements in the first preferred embodiment.

FIG. 2 shows a block diagram of the key components of the first preferred embodiment. The control panel (21) contains the LCD screen and the three x-ray expose buttons, male, female and calibration test. A push of the female button will reset the circuits and watchdog timer, and initiate the high voltage supply (30) to activate the HV and tube currents controls (28), which places high voltage across the x-ray tube (29). Several controls and readback circuits set values for mA, KV, and test for tube arching or temperature (34).

One embodiment showing eleven detectors (22) which are read out through amplifiers (23) to a sample and hold circuit (24) for analog to digital conversion in the 10 bit ADC. The main processor (25) such as the Motorola XC68 HC 916Y1 is the master control for the device. It controls the x-ray exposures, data readout, LCD display, QA checks and calculations. Data parameters are stored in the flash prom (26). RS232 serial data port is provided (27)

The electronic signals produced by the detectors ((22) are received by the computer processor (25) and stored in memory. It is desirable that one energy recording be stored sufficiently fast to allow the second energy recording without significant time lapse, such to minimize patient motion and patient radiation exposure.

The computer processor (25) controls the complete x-ray exposure sequence, detector readout, electronic processing, data display and communication. It preferably has the software program stored in permanent memory, such as flash memory or PROM. The electronic signals are stored temporarily for processing in DRAM. No disk storage devices are contemplated to further benefit simplicity, cost, and reliability.

Figure 3:
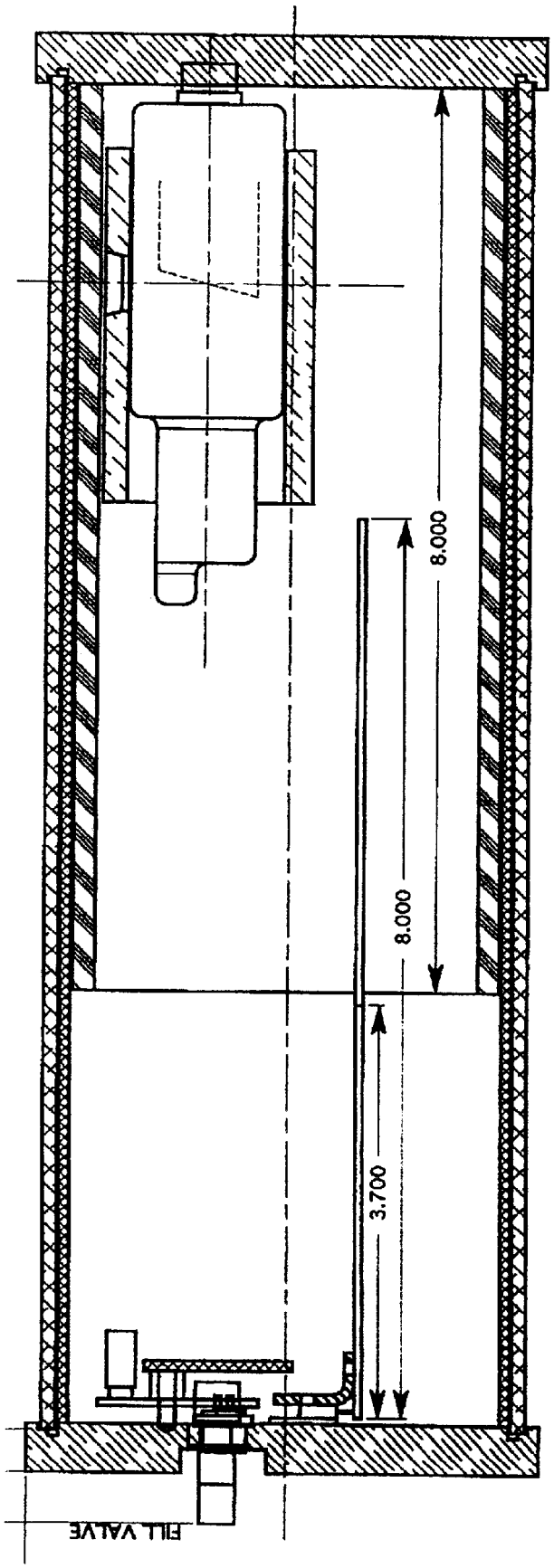
FIG. 3 shows one side view sketch of the x-ray source with shielded housing.

In FIG. 3 a preferred embodiment of the x-ray source is shown. A small fixed anode x-ray tube (30), high voltage board (31) integrated along with x-ray tube filament power supply and control electronics together forming the high voltage power supply. The x-ray source is integrated without high voltage cables and in the small space encased by a lead filled bronze container (32) which is filled with inert gas under pressure to serve as an electrical insulator. The absence of high voltage cables outside the x-ray source provides a high level of safety and simplicity of manufacturing. The gas insulator avoids using oil or silicon gels; both have the disadvantage of x-ray scatter and absorption in the material thickness present between the x-ray tube and tube port window (33). The gas, being of very low physical density, produces minimal x-ray scatter and attenuation. The x-ray port has an added absorbing metallic filter, preferable with a k-absorption edge at the preferred photon energy to improve energy separation in the beam spectra. The filter may be tin with a k-edge at 29 KeV. The filter is fixed in place to avoid requirements for moving it during the exposures.

Figure 4:
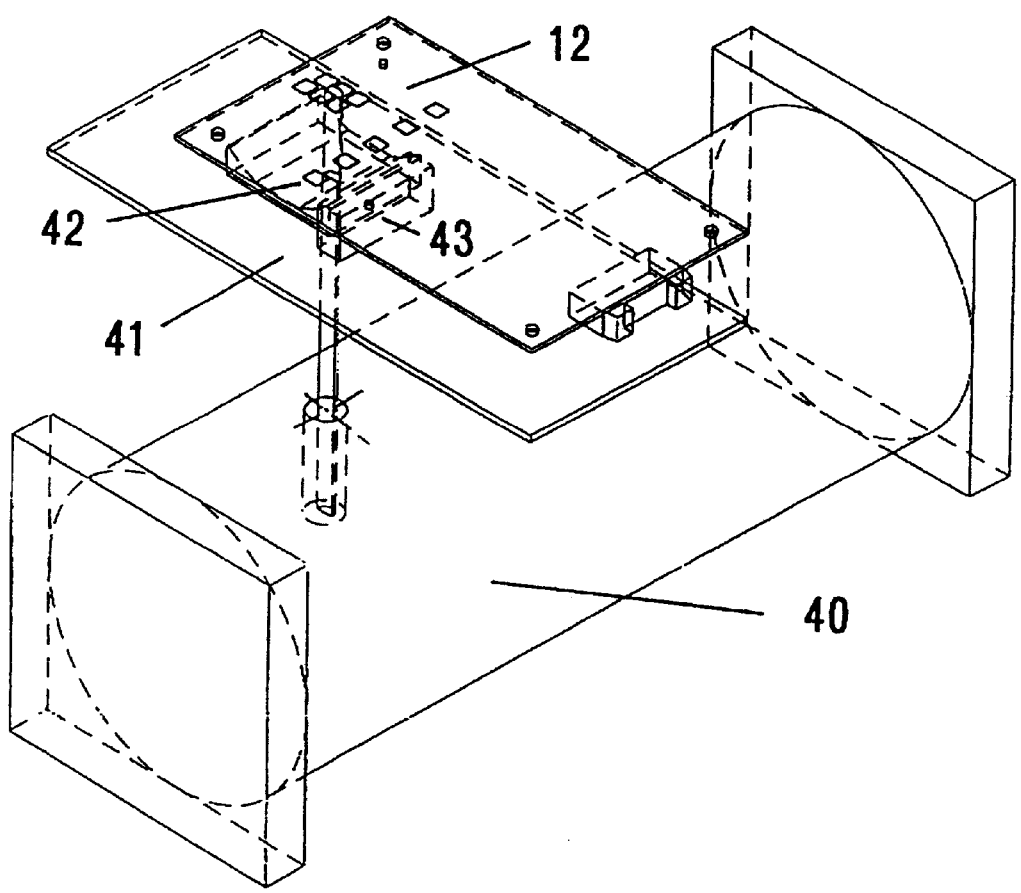
FIG. 4 shows the x-ray source, beam collimator with hand and phantom support surface, and detector board.

Referring now to FIG. 4, x-rays emerging from the x-ray source (40) impinge on the hand support (41) with an area, cone x-ray beam of small dimensions to just cover both the finger and calibration phantom simultaneously. The filter (42) is homogenous and of constant thickness and the primary collimation at the x-ray tube is positioned to pass the central ray from the tube target. X-rays near the heel of the tube target, the so-called heel effect, are collimated out of the used beam. The x-ray field at the hand support is therefore relatively flat in both intensity and effective energy, such that both the bones and the calibration phantom are exposed to similar effective beam energies in the same x-ray exposure. Placement of the bones and the phantom in close proximity greatly improves on this objective. Note that a constant x-ray beam over a large field or through large body parts or with the phantom placed at distance from the target bone would greatly reduce the effectiveness of the simultaneous calibration method. Use of the small finger bones, a small field of view, small phantom, and collimation from the central beam, all work to produce a consistent x-ray beam measured behind both the phantom and bones. The location of the calibration phantom (43) is fixed in place, such that with all patients and/or subsequent exposures, the beam energy will remain maximally consistent which greatly simplifies the automated software function. The x-ray detector board (12) is fixed in place relative to the beam and phantoms.

Figure 5:
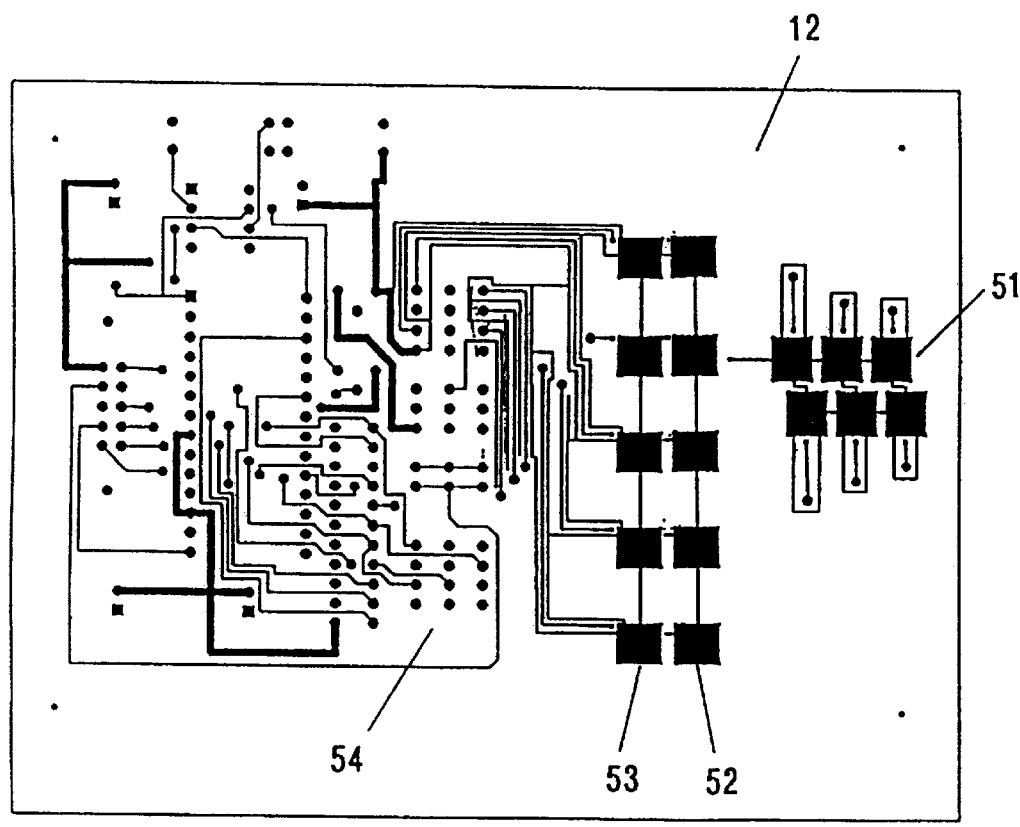
FIG. 5 shows the detector board layout in the first preferred embodiment, with discrete photodiode detectors.

FIG. 5 shows the detector board layout in the first preferred embodiment. Six photodiodes are positioned in two rows of three diodes each (51), offset spatially to each other. Representative diodes are 5×5 mm² silicon diodes from UDT Sensors, Hawthorne, Calif. The diodes have attached in permanent contact x-ray phosphor screens of CsI or GdOS. Other phosphors with different k-edge energies and light properties may be chosen for improved performance. The diode detectors are so positioned to cover the width of an average person's index finger. Specifically, the size and positioning will greatly ensure that at least one detector will be completely covered by bone. The line set of 5 diode detectors (52) are positioned to align with the steps of the bone equivalent calibration step wedge phantom. Likewise, the line of detector (53) is positioned behind the tissue equivalent step wedge.

The detector board also contains electronic signal conditioning circuits (54) for each detector, including a transimpedence amplifier followed by an integrator and a sample and hold amplifier with multiplexes for routing to the A/Dconverter.

Figure 6A:
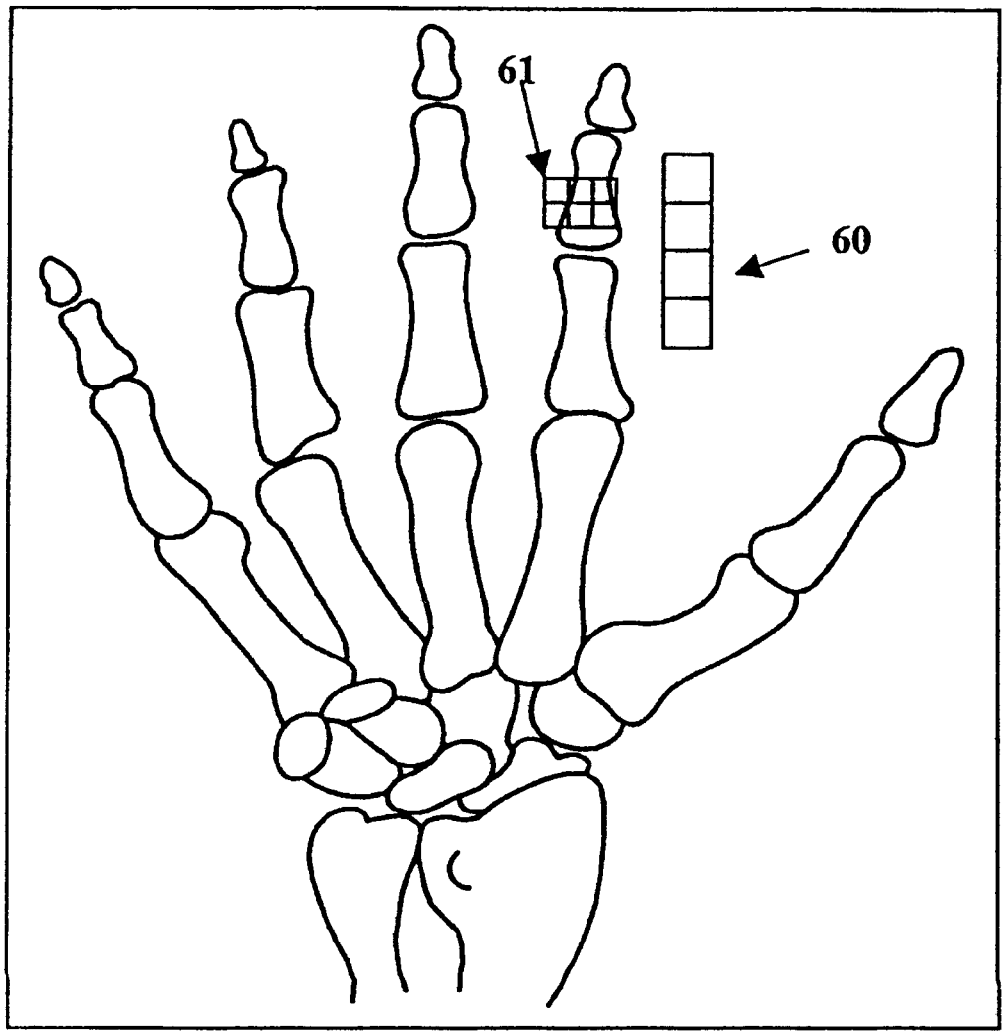
FIGS. 6A and 6B show the target bones (phalanges) and the positioning of the detectors above one phalanx, with the calibration phantom located adjacent to the phalanx.
Figure 6B:
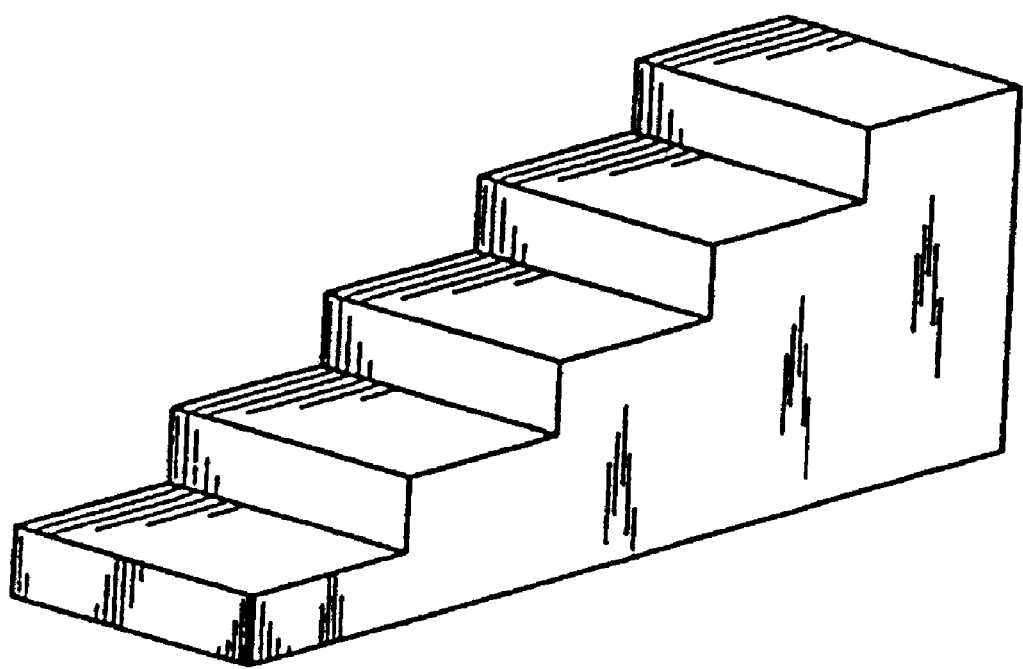

FIG. 6A shows a representation of the bones of the hand with a four-step calibration wedge (60) positioned adjacent to one phalanx (61) of the left hand. At least one detector of the set of 6 should be positioned behind bone in all cases. A side representation of a calibration phantom, FIG. 6B, shows four steps of bone equivalent material. Representative material is the tissue equivalent material, CT-water from Image Analysis of Columbia, Ky., with calcium hydroxyapatite homogeneously blended in known concentrations and thicknesses. Each phantom step has a known areal bone density, such as 0.15, 0.30, 0.45 and 0.60 gm/cm$^2$ of calcium hydroxyapatite which is chosen to cover the expected range of bone densities in human phalanges.

The phantom may have differing numbers of steps or a linear ramp of thicknesses of bone equivalent material. Aluminum or other bone mimicking material may be used for the reference, but preferably calcium hydroxyapatite in a tissue equivalent material is used for improved performance. The different effective thicknesses may be achieved by a step wedge of different thicknesses, with the material containing a fixed concentration of calcium material or, alternatively, a constant thickness may be used with varying concentrations of calcium material, as previously disclosed.

Figure 7:
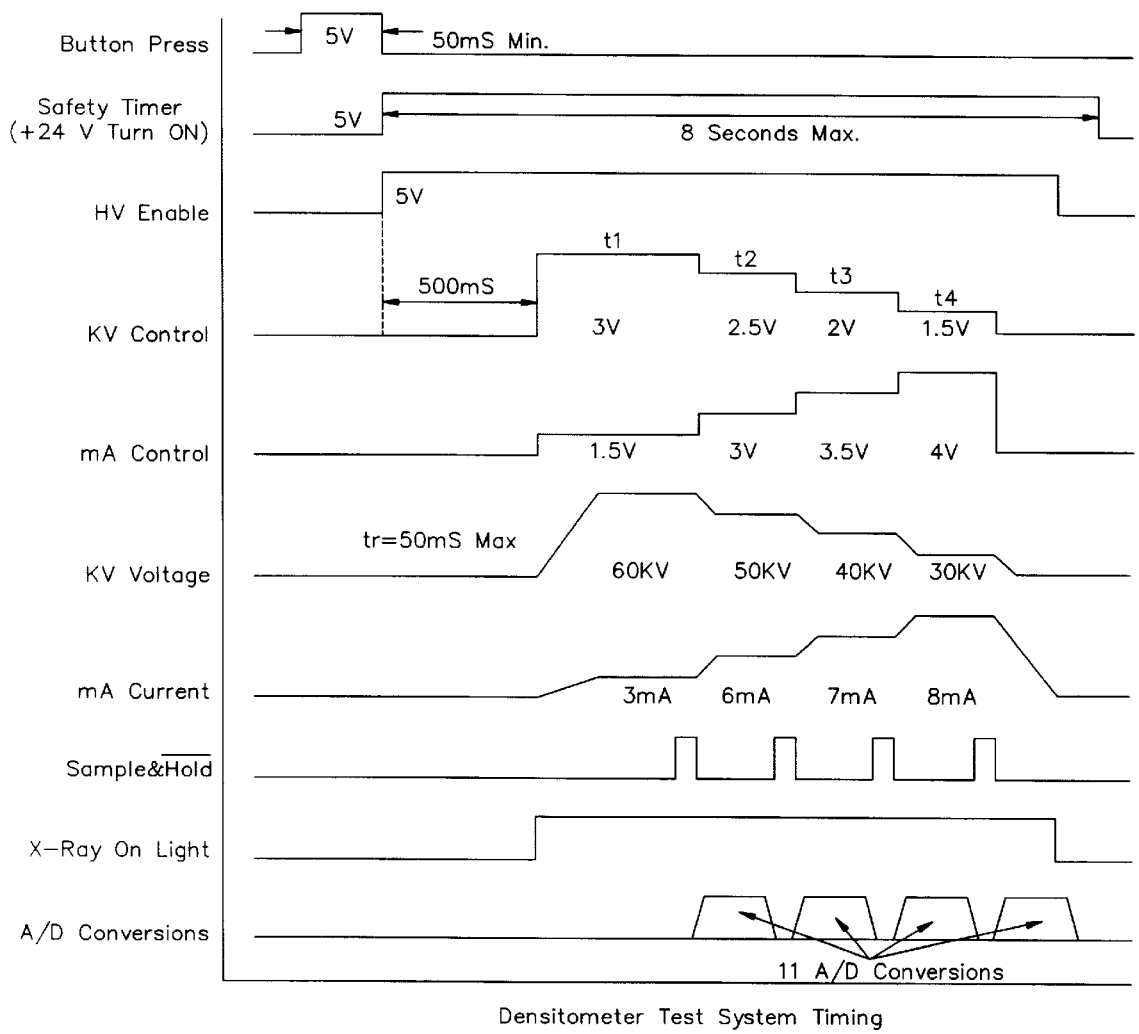
FIG. 7 shows the electronic time sequence of x-ray exposures and electronic recording events during one measurement sequence of the first embodiment.

FIG. 7 shows the electronic time sequence of x-ray exposures and signal digitization for the preferred embodiment employing four x-ray energies. When the exposure button is pressed, after a short response time of 50 milliseconds to boost the x-ray tube filament current, the high voltage is fired, typically at the highest kVp of say 60, and the first x-ray exposure at the first mA is initiated. The detector sample and hand amplifier records the signal and the data is read out through the A/C converter to memory. The high voltage and tube current are changed by the microprocessor and a second exposure and reading is made without shut off of the high voltage, and repeated at multiple kVps and tube currents. The circuit for a time out limit of 8 seconds is for safety and to protect against thermal overload of the tube.

Figure 8:
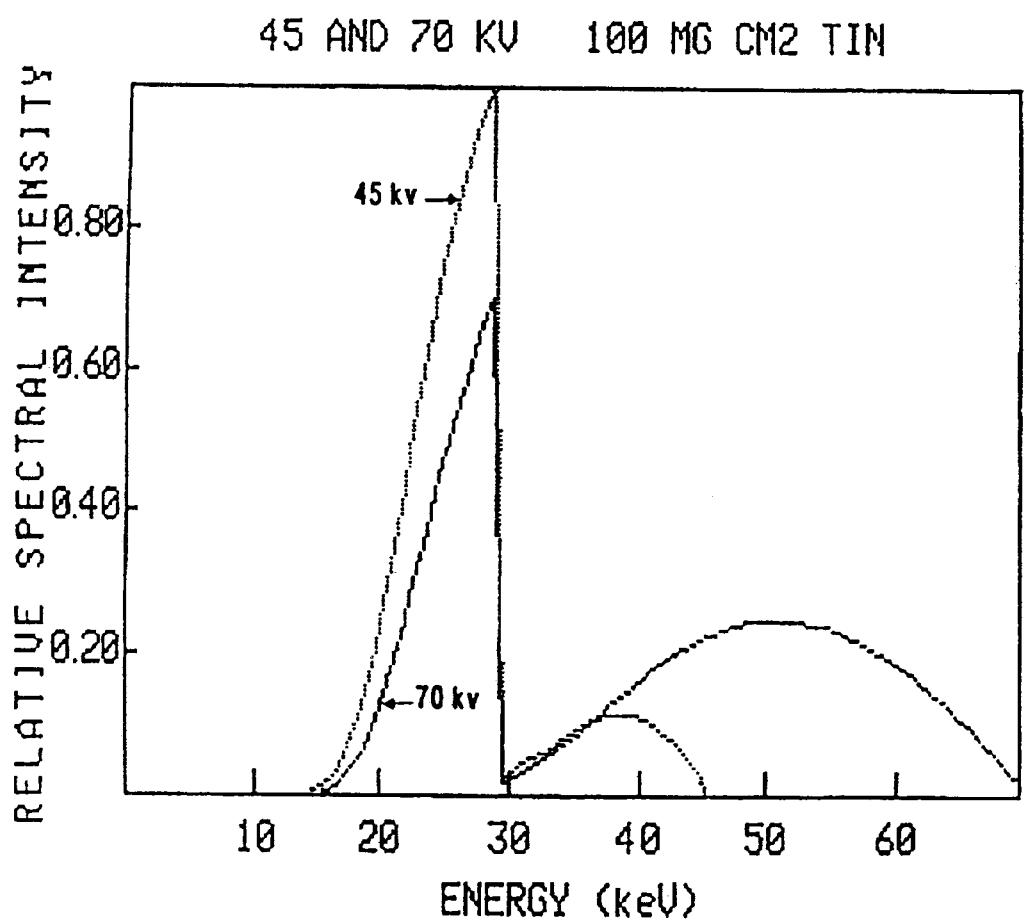
FIG. 8 shows calculated primary x-ray photon energy spectra for 45 kVp and 70 kVp, both filtered with 100 mg per $cm^2$ of tin.

FIG. 8 shows calculated primary x-ray photon energy spectra at 45 kVp and 70 kVp. Both spectra were filtered with 100 mg/cm$^2$ of tin. The k-edge absorption of tin is clearly shown. Low energy photons below about 20 KeV are effectively removed from the beam.

Figure 9:
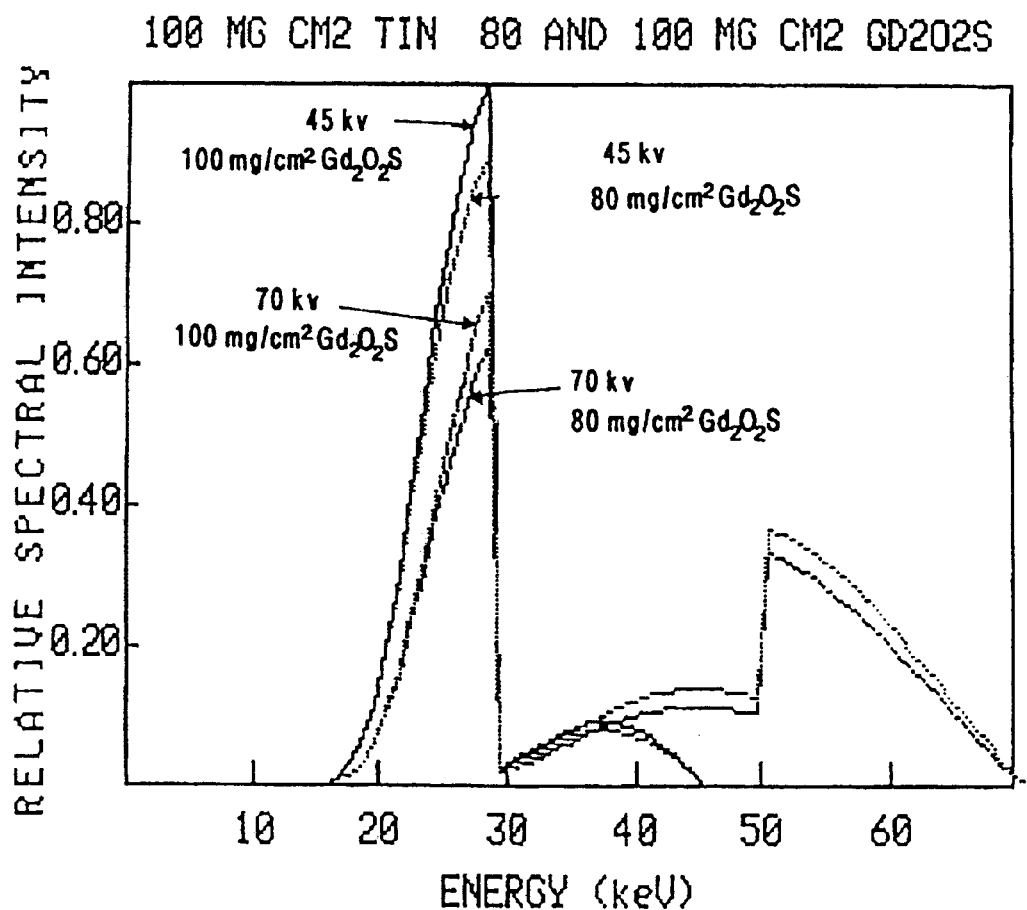
FIG. 9 shows absorbed x-ray energy spectra in 80 mg/$cm^2$ or 100 mg/$cm^2$ $Gd_2O_2S$ phosphor screens for the two spectra of FIG. 8.

FIG. 9 shows the absorbed x-ray photon spectra in $Gd_2O_2S$ phosphor screens of thickness 80 mg/cm$^2$ and 100 mg/cm$^2$. The absorption edge of gadolinium shows a sharp increase in absorbed energy above the k-edge for the 70 kVp spectrum. Use of the two kVps with tin filtration and the chosen phosphor effectively produces dual energy quasi-monoenergetic beam spectra. Effective beam energies of about 27 KeV and 55 KeV are achieved.

Figure 10A:
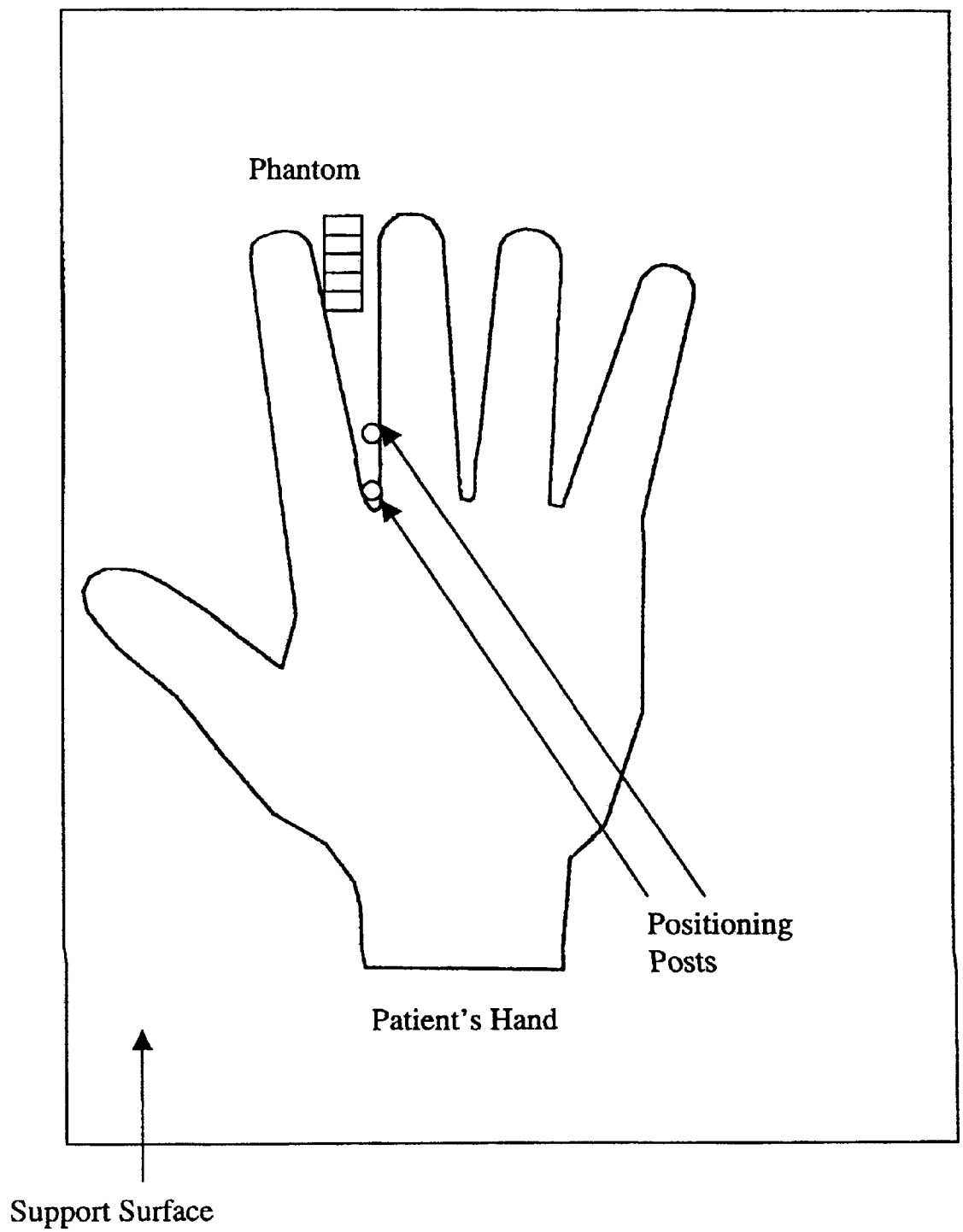
FIGS. 10a–c show different methods of positioning the hand and middle phalanx of the second digit.
Figure 10B:
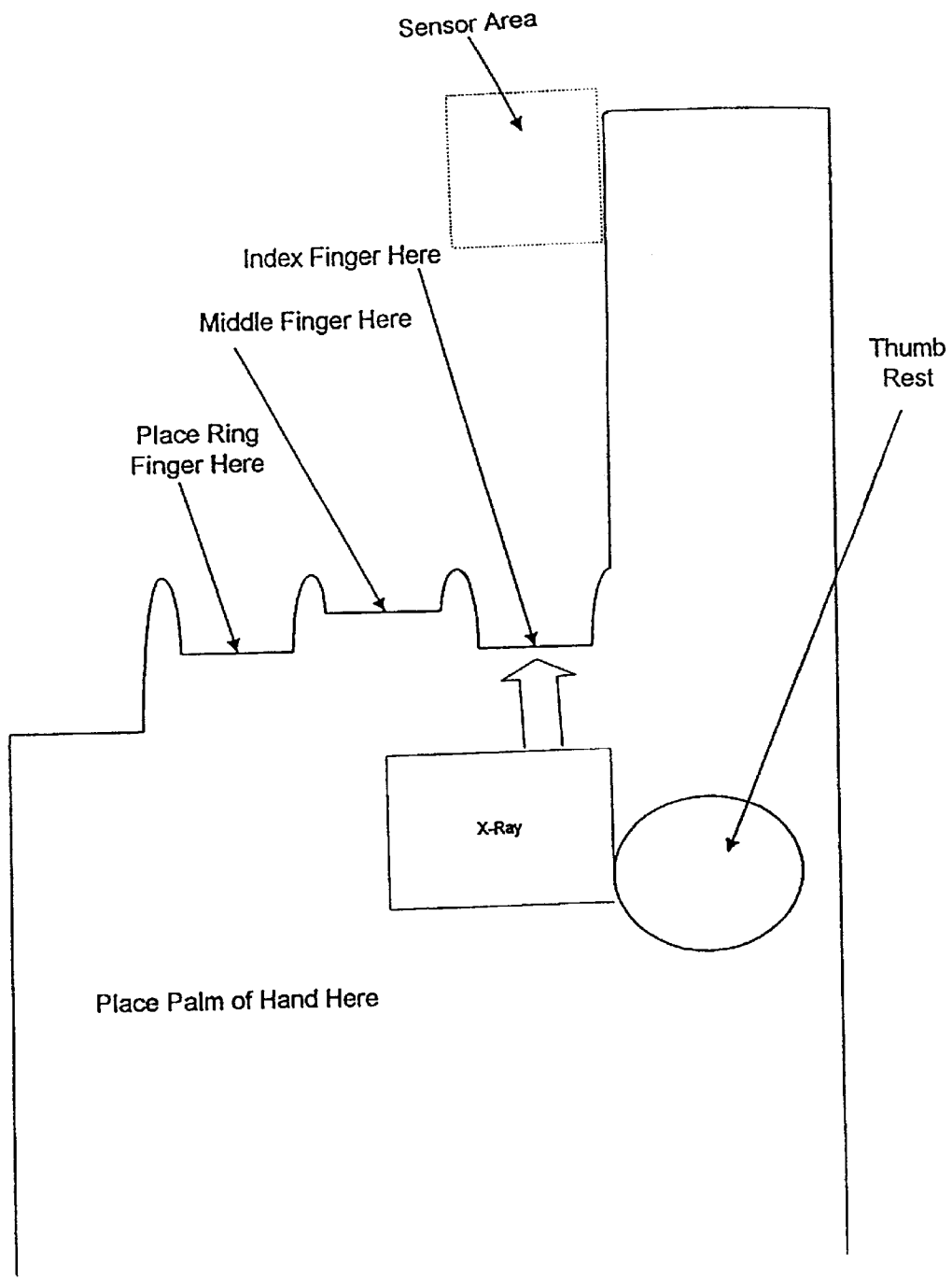
Figure 10C:
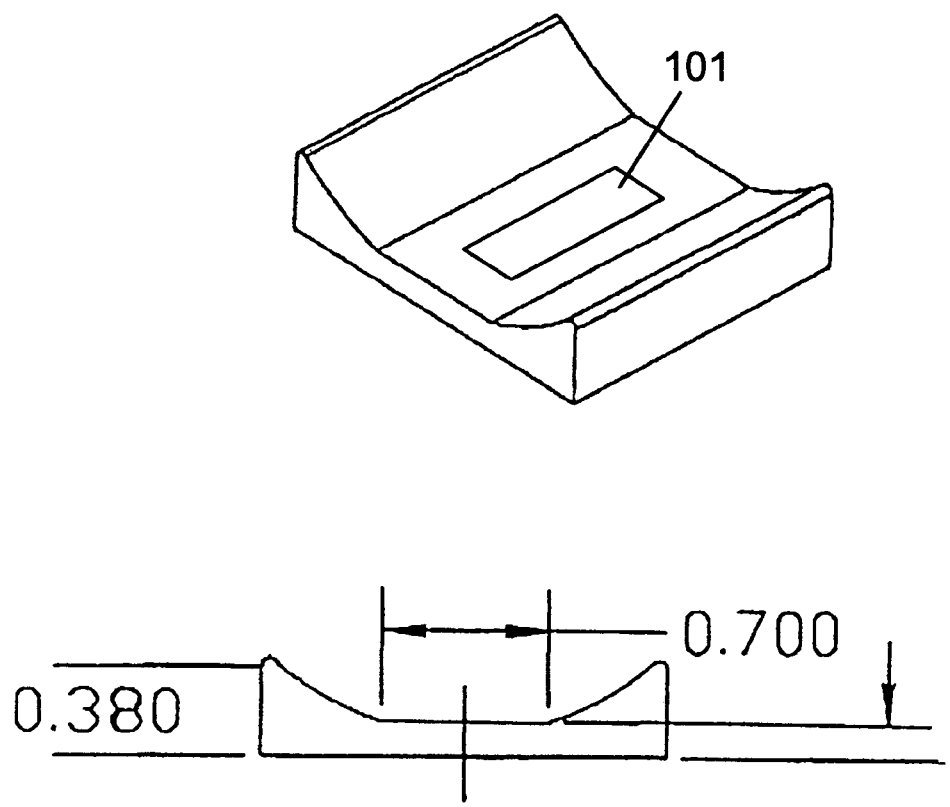

FIG. 10A shows the hand positioning support with calibration phantom and positioning posts. The patient's hand is positioned flat on the support, such that the post is located between the second and third digit of the left hand. The window under the target area of the bones and phantom is preferably of a low x-ray absorbing material such as thin aluminum, plastic, or carbon fiber material. This reduces unnecessary x-ray attenuation and scatter. The calibration phantom is positioned adjacent to the second digit, and at a location near the middle phalanx. Alternatively, the surface may be grooved with fitted channels for the fingers (10B) to facilitate reproducible hand positioning. An insert to the support surface containing a curved bottom to align the index finger (FIG. 10C) may further improve finger positioning, or if provided with an aperature (101), may even define the beam area, and, in the case of a large area detector, become the defining area for the bone density region of measurement for the calculation of areal density in g/cm$^2$.

Figure 11:
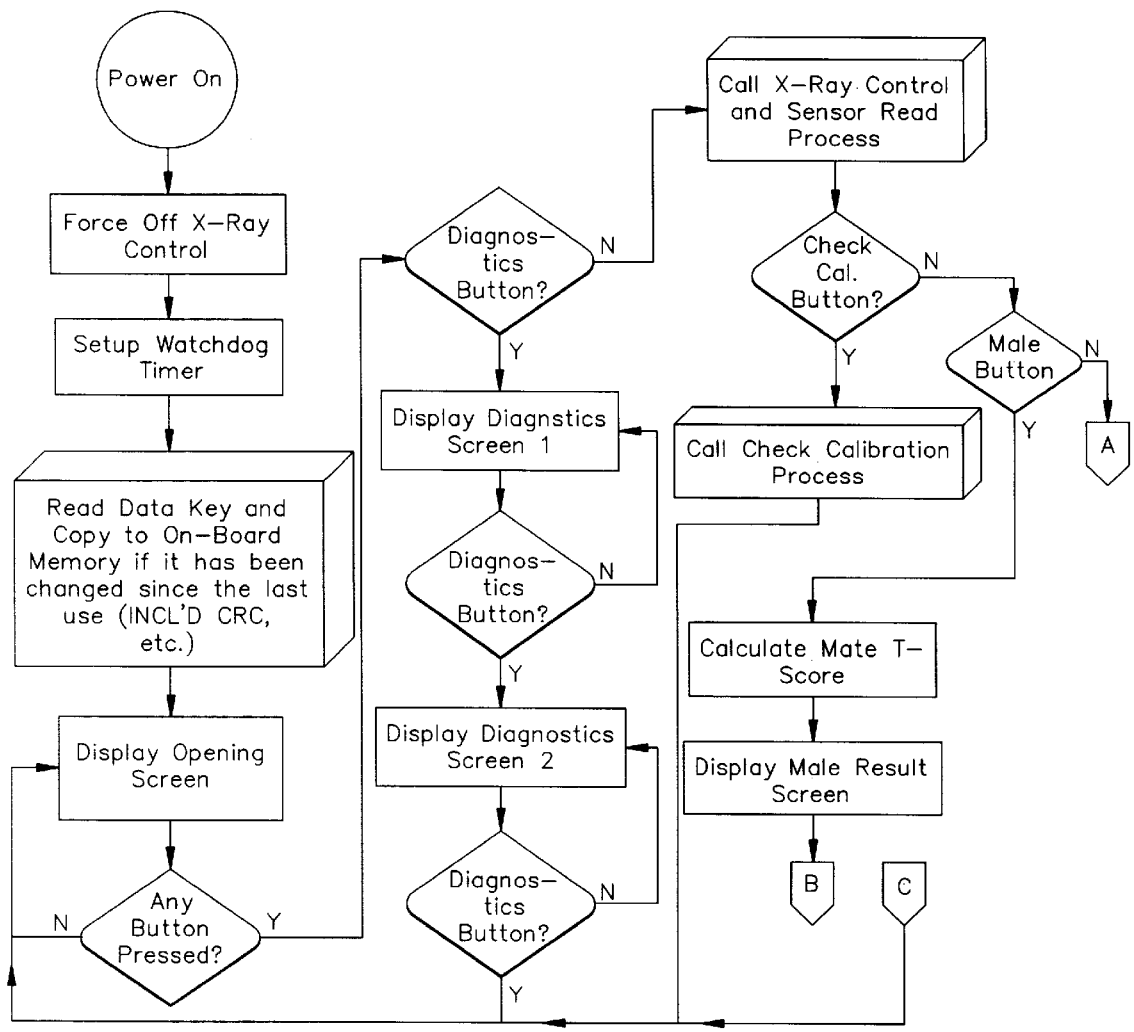
FIG. 11 shows the processing flow chart for the automated software in the diagnostic mode.

FIG. 11 shows the processing and display flow for the automated software in the diagnostic mode. The LCD display can be activated to display unprocessed data as well as diagnostic parameters indicative of device performance.

Figure 12A:
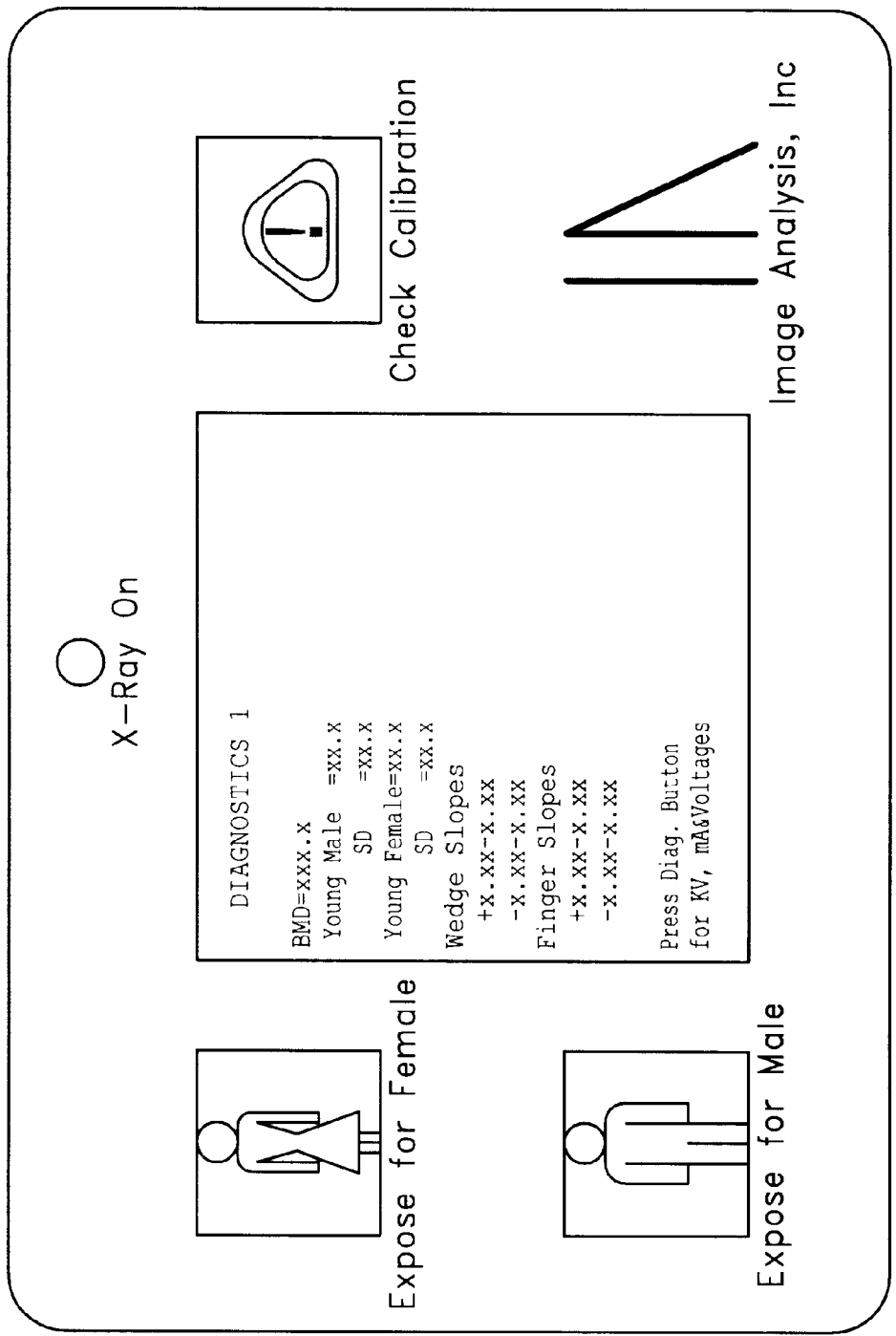
FIGS. 12A and B show two display screens on the LCD with measured quantities.

The diagnostics mode is intended to be used with a calibration plate. When the diagnostics button is pressed, the densitometer checks to see if a valid calibration check is available in the system memory. If it is not, the user is instructed to run a calibration check process. If calibration check data is available, the bone density is calculated and displayed on the diagnostics screen (FIG. 12A). In addition to the bone density, the display also includes the young normal reference bone density values that are currently in use. At the bottom of the first diagnostic screen is the measured wedge slopes and the finger sensor slopes.

Figure 12B:
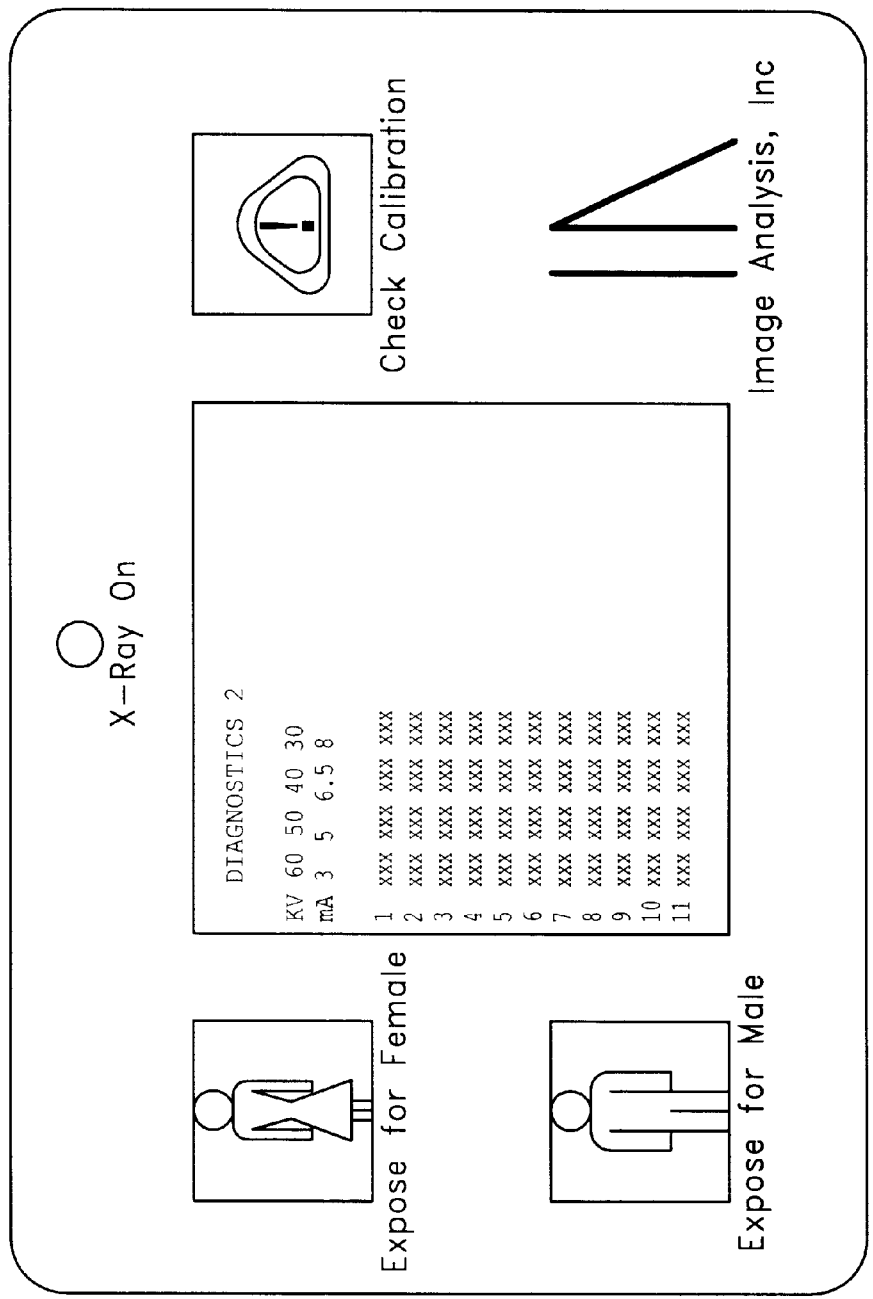

When the diagnostics button is pressed a second time, the second diagnostics screen is displayed (FIG. 12B). The Calibration Check function of the bone densitometer is intended to provide a method of determining if the x-ray and sensor systems are working correctly. The Calibration Check requires that the user install a "calibration plate", which is a separate QA phantom, into the patient exposure test area, and press the Calibration Check button. The test method described above is then executed. The software will begin by evaluating the results that were taken from the sensors in the test area. If all of these readings indicate that the sensors are in saturation, then the user will see an error screen telling them to install the calibration plate and re-expose the test.

Each x-ray exposure will generate readings from 11 different sensors. Five of these sensors are positioned above the calibration phantom (or wedge). The remaining six sensors are placed in the measurement area, above the patient's index finger. After all 44 measurements have been made and stored in temporary memory, a calibration algorithm is run, using the reference sensors readings. Another portion of the algorithm selects the finger sensor with the lowest detected signal to use as the patient data for the measurement being considered. The output of the algorithm is the bone density reading.

Several errors may occur during the life of the product. These errors may occur during any of the operating modes. The first error screen occurs when the user has overexposed the x-ray by making too many exposures in a specified period of time. The number of times and period of time used to make this decision are stored in memory. If the duty cycle is exceeded, the screen will display an error message.

Figure 13:
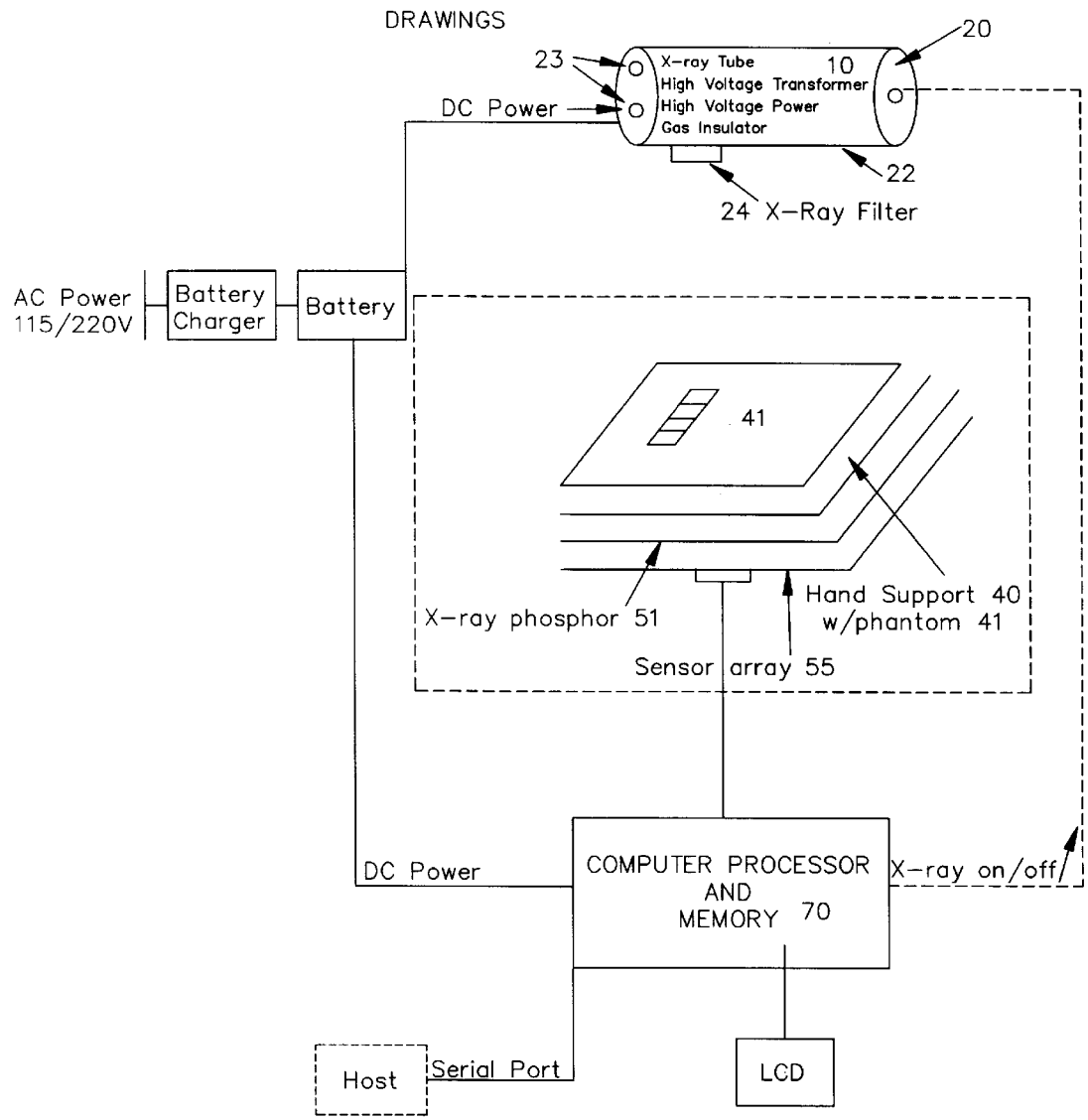
FIG. 13 is a schematic diagram showing the key elements in the second preferred embodiment of the invention showing an area imaging detector used to record images at two or more energies.

FIG. 13 shows a schematic drawing of the major components of the second preferred embodiment of the invention. X-rays are produced in x-ray source (14) and pass through the filter (42) before reaching the calibration wedge (57) and the finger (62). The x-ray phosphor screen (58) is mounted on the back side of the window of the hand support (56) The phosphor has an optically reflective backing, which reflects the emitted light back out one side of the screen. The reflective back is positioned against the hand support window to allow the x-ray generated light to escape the screen towards the sensor array (55). The phosphor may be any of several x-ray phosphors which generate light following x-ray absorption, but preferably will have a k-absorption edge of energy such to aid in the energy separation at the two energies. A phosphor of $Gd_2O_2S$ of 80 mg/cm$^2$ thickness, such as available from Kodak, may be used. The optimum thickness and particular phosphor depends on the x-ray energies used, and detector sensitivity to different light wavelengths and overall detector sensitivity. The phosphor needs to have fast decay time to avoid aftergrow, which could contribute to the second closely timed x-ray exposure. The sensor array (55) has an active area of size equal to the phosphor area and/or or the x-ray beam area when placed in direct contact with the phosphor. In this embodiment no lens or optical coupling is required. A lead glass or other x-ray absorber that can pass light may be placed between the phosphor and the sensor to preferably absorb x-rays which have passed through the screen without being absorbed. It is desirable that these x-rays not be absorbed directly by the sensor. The x-ray filter will pass the phosphor emitted light to the sensor with minimum reflections or absorption. The sensor array (55) may be formed of amorphous silicon with direct digital readout, such as the sensors of dPIX (Xerox) or EGG. The digital output signals can be read directly into the computer processor (13). These sensors have fast response time and pixel resolutions on the order of 124$\mu$ to a fraction of a mm, but of sufficient spatial discrimination to allow detection of bone edges and ROI placements in the phantom and bone images.

Alternatively the x-ray detector may be a phosphor as discussed above in combination with a reflective mirror, a focusing lens and a CCD array of dimensions smaller than the phosphor screen. Light emitted from the screen following x-ray exposure is reflected off the mirror towards the lens, which focuses the light to a dimension appropriate for the CCD array. The CCD, which is sensitive to primary x-rays, is preferably positioned out of the primary x-ray field. The lens can be a common, low cost lens, preferably with a low F-number. Alternatively, a bent fiber optic reducer may be used to couple the phosphor and CCD.

Yet another embodiment may use a direct x-ray sensitive detector (55). In this case, no x-ray phosphor is required since the detector absorbs the x-ray photons and directly produces an electrical signal. Detectors such as silicon diodes, CdTe arrays or other semiconductors can be used.

In the second embodiment complete two dimensional images are taken of the subject's finger simultaneously with the calibration wedge in place. Two images are taken at different beam energies, and are normalized by a scale factor of the pixel gray scale density at a specific location and area in the images before being subtracted.

Figure 14:
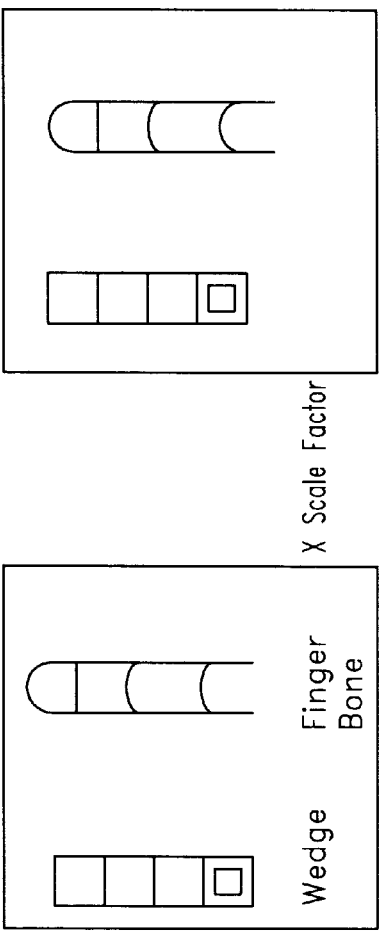
FIG. 14 shows a representation for the calibration wedge, a finger bone with ROI placements, and the calibration wedge curve.
Figure 14:
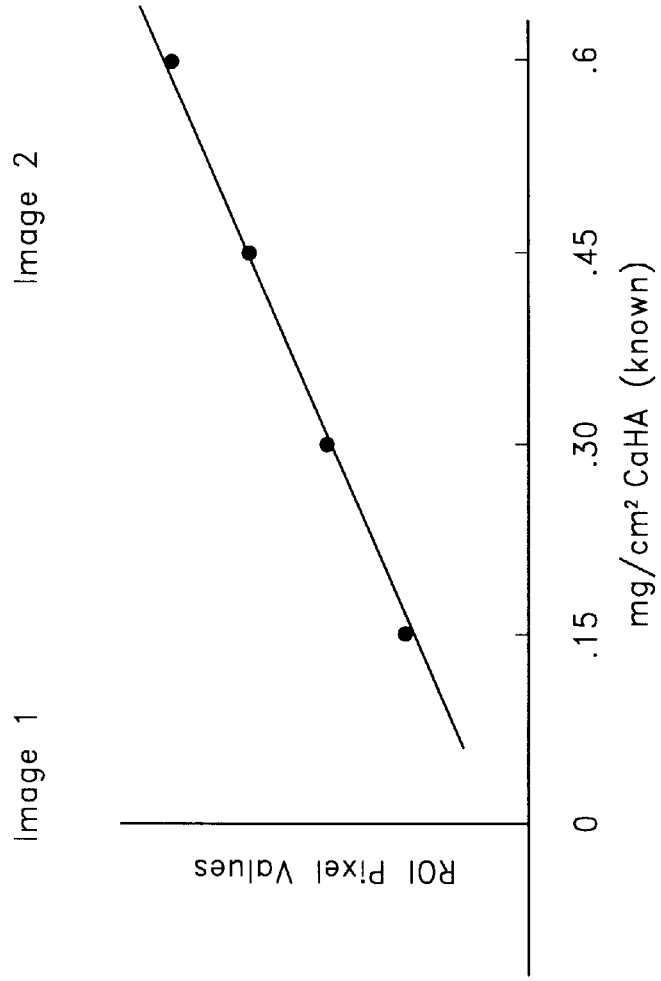
Figure 15:
FIG. 15 shows an x-ray image of the calibration wedge adjacent to a finger showing the phalanges.
Figure 15:
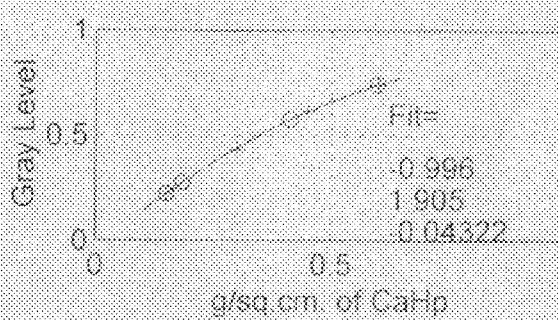
Figure 15:

Two images are taken back-to-back in approximately three seconds; one image at 60 kVp, and the second at 30 kVp. When the detector array reaches the desired signal level, the complete image frame is stored. The subtracted image of the bone is calibrated by the subtracted image of the step wedge with known bone density values for each step. The edges of the bone are automatically detected in software. Pixel intensities are calibrated using the calibration curve from the step wedge FIG. 14 shows a depiction of the calibration phantom with a representative ROI on the first wedge step. Representative detector readings behind each of 4 phantom steps are also shown in FIG. 14. Representative images of a patient's finger with the calibration wedge are shown in FIG. 15. The entire middle phalanx is outlined and measured in g/cm$^2$, and referenced to the bone equivalent wedge.

For example, the bone densitometer apparatus for evaluating a portion of a subject further comprises a stationary X-ray source emitting a beam of radiation of one or more energies, a reference calibration phantom exposed simultaneously with the subject being composed of substantially tissue equivalent material with respect to x-ray attenuation, the tissue equivalent material having calcium blended homogeneously therein and the phantom having one or more effective thicknesses providing one or more calibrations. This is accomplished by creating electronic representations of x-ray attenuation by the phantom and a portion of the subject's bone simultaneously from exposures of one or more energies using at least two discrete X-ray detectors, and comparing the electronic representations of the phantom and the portion of the subject to quantitatively determine bone density in the subject. The x-ray source can be an x-ray tube and x-ray generator. The detector selected may be a x-ray phosphor coupled to a discrete photodiode with electronic readout or a solid state semiconductor directly sensitive to x-rays. The bone densitometer may use a means of comparing by subtractions of two or more electronic representations taken with different x-ray energies.

One preferred bone densitometer provides for measurements on extremity body parts, wherein the densitometer consisting of an x-ray source, at least 2 x-ray detectors, a microprocessor, and a bone equivalent calibration phantom. The x-ray source produces at least three beam energies. The x-ray detectors and the x-ray source are fixed in position. The bone equivalent phantom are fixed in position and adjacent to the body part such that x-rays which pass through the body part do not also pass through the phantom. The bone densitometer being automated requires operation after x-ray exposure to produce at least three x-ray exposures of three different x-ray energies, each energy exposing simultaneously both the body part and the calibration phantom. Included are means to determine bone density in the body part in units equivalent to the calibration phantom. Thus, the bone densitometer requires no operation interaction after x-ray exposure to determine bone density. The x-ray source may optionally be integrated with the x-ray tube, high voltage transformer and control circuit enclosed within in an x-ray shielded container containing electrical insulation. The x-ray detector selected may be a flat panel detector with discrete elements formed of amorphous silicon coupled to an x-ray phosphor of same size which converts absorbed x-rays to light. The three x-ray exposures are achieved by changing the high voltage in three contiguous steps with a single high voltage power supply on and off cycle. The x-ray detector is a discrete photodiode of known area covered with an x-ray phosphor. The x-ray tube contains a fixed k-edge filter to shape the x-ray beam spectra, such as tin. The x-ray source, the processor and the detectors are powered from a battery.

In another embodiment, an X-ray Bone Densitometer for measuring bone density in a subject's body part comprises a stationary x-ray source capable of producing multiple x-ray energies, a reference calibration phantom composed of bone equivalent material of at least one thickness and one concentration. At least two discrete x-ray detectors are used wherein one of the detectors is positioned behind the calibration phantom such that x-rays are detected only after transmission through the phantom and at least one second detector positioned behind the subject's body part such that x-rays are detected only after transmission through the subject. Obtaining readings from a simultaneous exposure of both detectors from an x-ray exposure of the first energy and obtaining readings from a second simultaneous exposure of both detectors from a second x-ray exposure of second energy and obtaining readings from a third simultaneous exposure of both detectors of third energy, is repeated n times at n energies where n may be 2 or more. A support and positioning surface for the subject's body part provides for a support. The readings are compared to determine bone density in the subject. The phantom usually contains calcium hydroxyapatite and tissue equivalent materials; however, it could be aluminum. The detectors are discrete photodiodes with x-ray phosphor attached thereto, in contact with each other. The photodiode has an area of 5 mm by 5 mm, such area used to define the area of measurement for bone density. The x-ray source is an x-ray tube and x-ray power supply. A second calibration phantom of tissue equivalence is exposed simultaneously with the the bone equivalent phantom and the subject.

The bone densitometer provides for a method to measure bone density in a living subject using a radiation source and at least one radiation detector wherein the detector area contains a single discrete sensor, the detector has a sensitive area of at least 2×2 mm², the detector area defining the area of the bone measurement region of interest, the radiation detector is a photodiode with phosphor of known area, the radiation source is a radioactive isotope of one or more energies, and the radiation source is a fixed anode x-ray tube and high voltage power supply capable of producing at least one beam energy.

Furthermore, the bone densitometer provides for a method for measuring tissue density in a subject using a source of radiation of at least one x-ray energy, at least one detector, a collimating aperature and positioning structure for a portion of the subject. Preferably the radiation source, the detector, and the collimating aperature are fixed in position wherein the detector is of an area larger than the collimating aperature. The area of the aperature defines the measurement region of the portion of subject and included are means for comparing detector signals to determine tissue density. The tissue density provides a measure of fat content or if the tissue is bone. A preferred source of radiation is a radioactive isotope.

Another preferred embodiment for an x-ray bone densitometer for measuring bone density in a subject's bone, includes an x-ray source, at least two discrete x-ray detectors, a bone equivalent calibration wedge of at least one thickness, a tissue equivalent calibration wedge of at least one thickness. The device further comprises an x-ray collimation means to direct the x-rays onto the detectors and the subject, a structure to position subject's bone reproducibility adjacent to the calibration wedge and between the x-ray source and the detectors, a x-ray source wherein the x-ray detectors and the calibration wedge being fixed in position and stationary, wherein the x-ray detectors being large in area relative to imaging pixels, and the detector area defining the area of the measurement region of bone. The x-ray source provides three or more x-ray energies under microprocessor control. A microprocessor with data storage means is used to perform calculations and obtain readouts of the detectors. Means are included for determining bone density in the measurement regions of bone using the detector readouts from the calibration wedges and subject's bone. The automated operation can be initiated with a single push button. Readout methods display the measured bone density.

The foregoing detailed description is given primarily for clearness of understanding and no unnecessary limitations are to be understood therefrom, for modification will become obvious to those skilled in the art upon reading this disclosure and may be made without departing from the spirit of the invention and scope of the appended claims. Accordingly, this invention is not intended to be limited by the specific exemplifications presented hereinabove. Rather, what is intended to be covered is within the spirit and scope of the appended claims.

I claim:

1. A method to measure bone density in a living subject including the step of using a radiation source and at least one radiation detector area, wherein said detector area contains a single discrete sensor and wherein said detector has a sensitive area of at least 2×2 mm²; and wherein the area of the bone measurement region of interest is defined by said detector area.

2. The method of claim 1 wherein said radiation detector is a photo diode with phosphor of known area.

3. The method of claim 1 where said radiation source is a radioactive isotope of one or more energies.

4. The method of claim 1 where said radiation source is a fixed anode x-ray tube and high voltage power supply capable of producing at least one beam energy.

5. A dual energy X-ray bone densitometer, comprising:

a dual energy X-ray source;

a two dimensional area X-ray detector;

a bone equivalent calibration phantom; and a fixed aperture which limits X-rays to the anatomical site of measurement;

said X-ray source, said X-ray detector, and said calibration phantom being fixed in position such that the subject's anatomy to be analyzed and the calibration phantom are exposed simultaneously in one X-ray exposure of a first X-ray energy and exposed simultaneously in a second X-ray exposure of a second X-ray energy;

said detector producing quantitative electronic representations from detected X-rays which have penetrated said phantom or said subject's anatomy;

the subject's anatomy being positioned by the operator between said detector and said aperture to define the location of measurement regions; and a computer processor and operating software to determine bone density of the subject's anatomy in an electronic result.

6. A method for measuring tissue density in a subject using a source of radiation of at least one x-ray energy, at least one detector, a collimating aperture and positioning structure for a portion of said subject, wherein said radiation source, said detector, and said collimating aperture are fixed in position, said detector is of an area larger that said collimating aperture, wherein the area of said aperture defines the measurement region of said portion of subject, and means for comparing detector signals to determine tissue density.

7. The method of claim 6 where tissue density provides a measure of fat content.

8. The method of claim 6 where said tissue is bone.

9. A bone densitometer apparatus for evaluating a portion of a subject, comprising:

a stationary X-ray source emitting a beam of radiation of one or more energies;

a reference calibration phantom exposed simultaneously with said subject, being composed of substantially tissue equivalent material with respect to X-ray attenuation;

said tissue equivalent material having calcium blended homogeneously therein and said phantom having one or more effective thicknesses providing one or more calibrations, creating electronic representations of X-ray attenuation by the phantom and a portion of the subject's bone simultaneously from exposures of one or more energies using at least two discrete X-ray detectors;

the area of the portion of said subject to be measured being defined by the area of said discrete X-ray detectors; and comparing the electronic representations of the phantom and the portion of the subject to quantitatively determine bone density in the subject.

10. The bone densitometer of claim 9 wherein the x-ray source is an X-ray tube and X-ray generator.

11. The bone densitometer of claim 9, wherein said detector is a solid state semiconductor directly sensitive to X-rays.

12. The bone densitometer of claim 11, wherein said comparing is calculation of X-ray attenuation at multiple energies in said phantom and said subject.

13. A bone densitometer for measurements on extremity body parts, said densitometer consisting of an x-ray source, at least two x-ray detectors, a microprocessor, and a bone equivalent calibration phantom;

said x-ray source producing at least three beam energies;

said x-ray detectors and said x-ray source being fixed in position;

said bone equivalent phantom being fixed in position and adjacent to said body part such that x-rays which pass through the body part do not also pass through said phantom;

said bone densitometer being automated, thus requiring no operation after x-ray exposure;

producing at least three x-ray exposures of three different x-ray energies, each energy exposing simultaneously both said body part and said calibration phantom;

means to determine bone density in the body part in units equivalent to said calibration phantom; and said bone densitometer requiring no operation interaction after x-ray exposure to determine bone density.

14. The bone densitometer of claim 13, wherein the x-ray source is integrated with an x-ray tube, a high voltage transformer and a control circuit enclosed within an x-ray shielded container containing electric insulation.

15. The bone densitometer of claim 13 wherein each said x-ray detector is a flat panel detector with discrete elements formed of amorphous silicon coupled to an x-ray phosphor of same size which converts absorbed x-rays to light.

16. The bone densitometer of claim 13, wherein said three x-ray exposures are achieved by changing the high voltage in three contiguous steps with a single high voltage power supply on and off cycle.

17. The bone densitometer of claim 13, wherein each said x-ray detector is a discrete photo diode of known area covered with an x-ray phosphor.

18. The bone densitometer of claim 13, wherein said body part is the middle phalanx of the index finger of the left hand.

19. The bone densitometer of claim 13, wherein the x-ray tube contains a fixed k-edge filter to shape the x-ray beam spectra, such as tin.

20. The bone densitometer of claim 13 wherein said x-ray source, said processor and said detectors are powered from a battery.

21. An X-ray Bone Densitometer for measuring bone density in a subject's body part, comprising:

a support and positioning surface for the subject's body part;

a stationary x-ray source capable of producing multiple x-ray energies;

a reference calibration phantom composed of bone equivalent material of at least one thickness and one concentration; and at least two discrete x-ray detectors, one said detector positioned behind said calibration phantom such that x-rays are detected only after transmission through the phantom and at least one second detector positioned behind the subject's body part such that x-rays are detected only after transmission through the subject, said discrete x-ray detectors providing readings from a simultaneous exposure of both detectors from an x-ray exposure of a first energy and providing readings from a second simultaneous exposure of both detectors from a second x-ray exposure of a second energy, said simultaneous exposures repeated n times at n energies where n is at least 2, said readings compared to determine bone density in the subject.

22. The Bone Densitometer of claim 21, wherein said phantom contains calcium hydroxyapatite and tissue equivalent materials.

23. The Bone Densitometer of claim 21, wherein said phantom is aluminum.

24. The Bone Densitometer of claim 21, wherein said detectors are discrete photo diodes with X-ray phosphor attached thereto, in contact with each other.

25. The Bone Densitometer of claim 24 wherein each one of said photo diodes has an area of 5 mm by 5 mm, such area used to define the area of measurement for bone density.

26. The Bone Densitometer of claim 21, wherein said x-ray source is an x-ray tube and x-ray power supply.

27. The Bone Densitometer of claim 21, wherein a second calibration phantom of tissue equivalence is exposed simultaneously with the said bone equivalent phantom and said subject.

28. The Bone Densitometer of claim 21 wherein said bone equivalent phantom has four step thicknesses and four discrete detectors positioned behind said steps.

29. The method of claim 6 where said source of radiation is a radioactive isotope.

30. An x-ray bone densitometer for measuring bone density in a subject's bone, including an x-ray source, at least two discrete x-ray detectors, a bone equivalent calibration wedge of at least one thickness, a tissue equivalent calibration wedge of at least one thickness, further comprising:

an x-ray collimation means to direct the x-rays onto said detectors and said subject;

a structure to position a subject's bone reproducibly adjacent to said calibration wedge and between said x-ray source and said detectors;

said x-ray source, said x-ray detectors and said calibration wedge being fixed in position and stationary;

said x-ray detectors being large in area relative to imaging pixels, said detector area defining the area of the measurement region of bone;

said x-ray source providing three or more x-ray energies under microprocessor control;

a microprocessor with data storage means to perform calculations and obtain readouts of said detectors;

means for determining bone density in said measurement regions of bone using said detector readouts from said calibration wedges and subject's bone;

a single push button to initiate automated operation; and a readout to display the measured bone density.

* * * * *